US00RE50915E

(19) United States
(12) Reissued Patent
Bosshard et al.

(10) Patent Number: US RE50,915 E
(45) Date of Reissued Patent: Jun. 16, 2026

(54) THREADED LOCKING STRUCTURES FOR AFFIXING BONE ANCHORS TO A BONE PLATE, AND RELATED SYSTEMS AND METHODS

(71) Applicant: DePuy Synthes Products, Inc., Raynham, MA (US)

(72) Inventors: Simon M. Bosshard, Bern (CH); Michael McGurk, Williamstown, NJ (US); Mirko Rocci, Bettlach (CH); Stefan Dude, Neuendorf (CH)

(73) Assignee: DePuy Synthes Products, Inc., Raynham, MA (US)

(21) Appl. No.: 18/200,660

(22) Filed: May 23, 2023

Related U.S. Patent Documents

Reissue of:
(64) Patent No.: 11,013,541
Issued: May 25, 2021
Appl. No.: 15/966,047
Filed: Apr. 30, 2018

(51) Int. Cl.
*A61B 17/80* (2006.01)

(52) U.S. Cl.
CPC ..... *A61B 17/8057* (2013.01)

(58) Field of Classification Search
None
See application file for complete search history.

(56) References Cited

U.S. PATENT DOCUMENTS

| | | | |
|---|---|---|---|
| 327,296 | A | 9/1885 | Mcginnis |
| 1,105,105 | A | 7/1914 | Sherman |
| 1,203,546 | A | 10/1916 | Parsons |
| 2,228,584 | A | 1/1941 | Piace |

(Continued)

FOREIGN PATENT DOCUMENTS

| | | | |
|---|---|---|---|
| AU | 2004245023 | A1 | 12/2004 |
| CA | 1112803 | A | 11/1981 |

(Continued)

OTHER PUBLICATIONS

Printout from USFDA 510(k) Premarket Notification Database, dated May 23, 2007, listing Synthes Distal Femur Plate (DFP) System, and bearing 510(k) No. K982222 (attached as Exhibit N to Amended Answer.

(Continued)

*Primary Examiner* — Glenn K Dawson
(74) *Attorney, Agent, or Firm* — BakerHostetler

(57) ABSTRACT

A bone plate includes at least one hole extending through the bone plate from an upper plate surface to a lower plate surface along a central hole axis that is oriented along an axial direction. The at least one hole defined by an interior surface of the bone plate. The interior surface further defining a plurality of columns sequentially located about a circumference of the interior surface and a plurality of recesses located circumferentially between the columns. Each of the columns defines a plurality of thread segments each defining a root, a first thread surface extending from the root to a first crest, and a second thread surface extending from the root to a second crest. At least a portion of the first and second thread surfaces are offset from one another at a thread angle. The thread angle of at least one of the thread segments is in a range of about 5 degrees to about 59 degrees.

36 Claims, 22 Drawing Sheets

(56) References Cited

U.S. PATENT DOCUMENTS 2,352,297 A 6/1944 Wales
2,414,882 A 1/1947 Longfellow
2,443,363 A 6/1948 Kenneth et al.
2,477,430 A 7/1949 Swanstrom
2,496,126 A 1/1950 Haboush
2,526,959 A 10/1950 Lorenzo
2,612,159 A 9/1952 Collison
2,627,855 A 2/1953 Price
2,699,774 A 1/1955 Livingston
2,772,676 A 12/1956 Pohl
2,801,631 A 8/1957 Charnley
2,846,701 A 8/1958 Bedford, Jr.
2,874,691 A 2/1959 Mason
3,025,853 A 3/1962 Mason
3,229,743 A 1/1966 Derby
3,263,949 A 8/1966 Conrad
3,314,326 A 4/1967 Bedford, Jr.
3,364,807 A 1/1968 Holton
3,374,786 A 3/1968 Callender, Jr.
3,388,732 A 6/1968 Holton
3,463,148 A 8/1969 Treace
3,489,143 A 1/1970 Halloran
3,534,731 A 10/1970 Muller
3,551,389 A 12/1970 Prince, Jr.
3,552,389 A 1/1971 Allgower et al.
3,561,437 A 2/1971 Orlich
3,577,601 A 5/1971 Mariani et al.
3,630,261 A 12/1971 Gley
3,668,972 A 6/1972 Allgower et al.
3,688,972 A 9/1972 Mahon
3,695,259 A 10/1972 Yost
3,695,618 A 10/1972 Woolley et al.
3,716,050 A 2/1973 Johnston
3,741,205 A 6/1973 Markolf et al.
3,744,488 A 7/1973 Cox
3,779,240 A 12/1973 Kondo
3,782,374 A 1/1974 Fischer
3,824,995 A 7/1974 Getscher et al.
3,842,825 A 10/1974 Wagner
3,877,339 A 4/1975 Muenchinger
RE28,841 E 6/1976 Martin et al.
3,967,049 A 6/1976 Brandt
3,996,834 A 12/1976 Reynolds
3,996,931 A 12/1976 Callender, Jr.
4,009,712 A 3/1977 Burstein et al.
4,029,091 A 6/1977 Von et al.
4,040,129 A 8/1977 Steinemann et al.
4,095,591 A 6/1978 Graham et al.
4,120,298 A 10/1978 Fixel
4,172,452 A 10/1979 Forte et al.
4,175,555 A 11/1979 Herbert
4,219,015 A 8/1980 Steinemann
4,236,512 A 12/1980 Aginsky
4,263,904 A 4/1981 Judet
4,269,180 A 5/1981 Dall et al.
4,304,039 A 12/1981 Asmus
4,338,926 A 7/1982 Kummer et al.
4,355,198 A 10/1982 Gartland, Jr.
4,379,451 A 4/1983 Getscher
4,388,921 A 6/1983 Sutter et al.
4,408,601 A 10/1983 Wenk
4,429,690 A 2/1984 Angelino-Pievani
4,438,762 A 3/1984 Kyle
4,454,876 A 6/1984 Mears
RE31,628 E 7/1984 Allgower et al.
4,484,570 A 11/1984 Sutter et al.
4,484,750 A 11/1984 Scruggs
4,488,543 A 12/1984 Tornier
4,491,317 A 1/1985 Bansal
4,493,317 A 1/1985 Klaue
4,494,535 A 1/1985 Haig
4,513,744 A 4/1985 Klaue
4,537,185 A 8/1985 Stednitz
4,565,193 A 1/1986 Streli
4,580,225 A 4/1986 Thompson
4,612,920 A 9/1986 Lower
4,612,923 A 9/1986 Kronenthal
4,616,638 A 10/1986 Griggs
4,617,922 A 10/1986 Griggs
4,621,629 A 11/1986 Koeneman
4,628,923 A 12/1986 Medoff
4,629,455 A 12/1986 Kanno
4,630,985 A 12/1986 Simons
4,651,724 A 3/1987 Berentey et al.
4,657,001 A 4/1987 Fixel
4,683,878 A 8/1987 Carter
4,717,613 A 1/1988 Ottaviano
4,747,613 A 5/1988 Brichoud et al.
4,776,329 A 10/1988 Treharne
4,776,330 A 10/1988 Chapman et al.
4,781,183 A 11/1988 Casey et al.
4,791,918 A 12/1988 Von Hasselbach
4,794,918 A 1/1989 Wolter
4,795,473 A 1/1989 Grimes
4,800,874 A 1/1989 David et al.
4,838,252 A 6/1989 Klaue
4,848,328 A 7/1989 Laboureau et al.
4,858,601 A 8/1989 Glisson
4,867,144 A 9/1989 Karas et al.
4,903,691 A 2/1990 Heinl
4,905,680 A 3/1990 Tunc
4,927,421 A 5/1990 Goble et al.
4,955,886 A 9/1990 Pawluk
4,957,496 A 9/1990 Schmidt
4,957,497 A 9/1990 Hoogland et al.
4,964,403 A 10/1990 Karas et al.
4,966,599 A 10/1990 Pollock
4,973,332 A 11/1990 Kummer
4,973,333 A 11/1990 Treharne
4,988,350 A 1/1991 Herzberg
5,002,544 A 3/1991 Klaue et al.
5,006,120 A 4/1991 Carter
5,013,313 A 5/1991 Surer
5,013,315 A 5/1991 Barrows
5,015,248 A 5/1991 Burstein et al.
5,027,904 A 7/1991 Miller et al.
5,039,265 A 8/1991 Rath et al.
5,041,113 A 8/1991 Biedermann et al.
5,041,114 A 8/1991 Chapman et al.
5,041,116 A 8/1991 Wilson
5,053,036 A 10/1991 Perren et al.
5,085,660 A 2/1992 Lin
5,087,260 A 2/1992 Fixel
5,108,399 A 4/1992 Eitenmuller et al.
5,108,449 A 4/1992 Gray
5,116,336 A 5/1992 Frigg
5,127,914 A 7/1992 Calderale et al.
5,129,901 A 7/1992 Decoste
5,139,497 A 8/1992 Tilghman et al.
5,147,361 A 9/1992 Ojima et al.
5,147,363 A 9/1992 Haerle
5,151,103 A 9/1992 Tepic et al.
5,152,794 A 10/1992 Davidson
5,190,544 A 3/1993 Chapman et al.
5,197,966 A 3/1993 Sommerkamp
5,201,733 A 4/1993 Etheredge, III
5,261,910 A 11/1993 Warden et al.
5,269,784 A 12/1993 Mast
5,275,601 A 1/1994 Gogolewski et al.
5,290,281 A 3/1994 Tschakaloff
5,300,074 A 4/1994 Frigg
5,304,180 A 4/1994 Slocum
5,306,275 A 4/1994 Bryan
5,324,290 A 6/1994 Zdeblick et al.
5,324,292 A 6/1994 Meyers
5,336,224 A 8/1994 Selman
5,356,410 A 10/1994 Pennig
5,360,429 A 11/1994 Jeanson et al.
5,360,448 A 11/1994 Thramann
5,364,398 A 11/1994 Chapman et al.
5,364,399 A 11/1994 Lowery et al.
5,372,598 A 12/1994 Luhr et al.
5,376,126 A 12/1994 Lin
5,395,372 A 3/1995 Holt et al.

(56) References Cited

U.S. PATENT DOCUMENTS 5,403,136 A 4/1995 Mathys
5,413,577 A 5/1995 Pollock
5,429,641 A 7/1995 Gotfried
5,433,719 A 7/1995 Pennig
5,458,654 A 10/1995 Tepic
5,462,547 A 10/1995 Weigum
5,484,439 A 1/1996 Olson et al.
5,514,138 A 5/1996 McCarthy
5,520,690 A 5/1996 Errico et al.
5,522,902 A 6/1996 Yuan et al.
5,531,746 A 7/1996 Errico et al.
5,534,032 A 7/1996 Hodorek
5,558,674 A 9/1996 Heggeness et al.
5,569,248 A 10/1996 Mathews
5,571,109 A 11/1996 Bertagnoli
5,571,198 A 11/1996 Drucker et al.
5,586,985 A 12/1996 Putnam et al.
5,591,168 A 1/1997 Judet et al.
5,601,551 A 2/1997 Taylor et al.
5,601,553 A 2/1997 Trebing et al.
5,607,426 A 3/1997 Ralph et al.
5,607,427 A 3/1997 Tschakaloff
5,607,428 A 3/1997 Lin
5,620,445 A 4/1997 Brosnahan et al.
5,647,872 A 7/1997 Gilbert et al.
5,655,089 A 8/1997 Bucci
5,658,339 A 8/1997 Tronzo et al.
5,662,655 A 9/1997 Laboureau et al.
5,674,222 A 10/1997 Berger et al.
5,676,667 A 10/1997 Hausman
5,681,311 A 10/1997 Foley et al.
D385,963 S 11/1997 Hansson
5,690,633 A 11/1997 Taylor et al.
5,693,055 A 12/1997 Zahiri et al.
5,702,396 A 12/1997 Hoenig et al.
5,702,399 A 12/1997 Kilpela et al.
5,709,682 A 1/1998 Medoff
5,709,686 A 1/1998 Talos et al.
5,709,687 A 1/1998 Pennig
5,718,704 A 2/1998 Medoff
5,718,705 A 2/1998 Sammarco
5,728,099 A 3/1998 Tellman et al.
5,733,287 A 3/1998 Tepic et al.
5,735,853 A 4/1998 Olerud
5,741,256 A 4/1998 Bresina
5,741,258 A 4/1998 Klaue et al.
5,743,912 A 4/1998 Lahille et al.
5,749,872 A 5/1998 Kyle et al.
5,766,175 A 6/1998 Martinotti
5,772,662 A 6/1998 Chapman et al.
5,779,706 A 7/1998 Tschakaloff
5,785,713 A 7/1998 Jobe
5,797,916 A 8/1998 McDowell
5,800,553 A 9/1998 Albrektsson et al.
5,810,821 A 9/1998 Vandewalle
5,810,822 A 9/1998 Mortier
5,810,823 A 9/1998 Klaue et al.
5,827,286 A 10/1998 Incavo et al.
5,853,413 A 12/1998 Carter et al.
5,921,988 A 7/1999 Legrand
5,928,084 A 7/1999 Green
5,931,801 A 8/1999 Burbank et al.
5,931,839 A 8/1999 Medoff
5,938,664 A 8/1999 Winquist et al.
5,954,722 A 9/1999 Bono
5,961,524 A 10/1999 Crombie
5,968,046 A 10/1999 Castleman
5,968,047 A 10/1999 Reed
5,973,223 A 10/1999 Tellman et al.
5,976,139 A 11/1999 Bramlet
5,976,141 A 11/1999 Haag et al.
5,989,255 A 11/1999 Pepper et al.
5,999,940 A 12/1999 Ranger
6,001,099 A 12/1999 Huebner
6,007,535 A 12/1999 Rayhack et al.
6,022,352 A 2/2000 Vandewalle
6,030,162 A 2/2000 Huebner
6,030,389 A 2/2000 Wagner et al.
6,059,785 A 5/2000 Schavan et al.
6,066,141 A 5/2000 Dall et al.
6,096,040 A 8/2000 Esser
6,113,603 A 9/2000 Medoff
6,129,728 A 10/2000 Schumacher et al.
6,129,730 A 10/2000 Bono et al.
6,152,927 A 11/2000 Farris et al.
6,155,756 A 12/2000 Mericle et al.
6,183,474 B1 2/2001 Bramlet et al.
6,183,475 B1 2/2001 Lester et al.
6,187,007 B1 2/2001 Frigg et al.
6,206,881 B1 3/2001 Frigg et al.
6,221,073 B1 4/2001 Weiss et al.
6,221,075 B1 4/2001 Toermala et al.
D443,060 S 5/2001 Benirschke et al.
6,224,602 B1 5/2001 Hayes
6,228,085 B1 5/2001 Theken et al.
6,235,032 B1 5/2001 Link
6,235,033 B1 5/2001 Brace et al.
6,258,250 B1 7/2001 Weissenbacher et al.
6,261,291 B1 7/2001 Talaber et al.
6,283,969 B1 9/2001 Grusin et al.
6,287,309 B1 9/2001 Baccelli et al.
6,290,703 B1 9/2001 Ganem
6,306,136 B1 10/2001 Baccelli
6,306,140 B1 10/2001 Siddiqui
6,322,562 B1 11/2001 Wolter
6,325,803 B1 12/2001 Schumacher et al.
6,338,734 B1 1/2002 Burke et al.
6,342,055 B1 1/2002 Eisermann et al.
6,348,052 B1 2/2002 Sammarco
6,350,265 B1 2/2002 Blaustein et al.
6,355,041 B1 3/2002 Martin
6,355,042 B2 3/2002 Winquist et al.
6,358,250 B1 3/2002 Orbay
6,364,882 B1 4/2002 Orbay
6,375,657 B1 4/2002 Doubler et al.
6,379,359 B1 4/2002 Dahners
D458,374 S 6/2002 Bryant et al.
D458,683 S 6/2002 Bryant et al.
D458,684 S 6/2002 Bryant et al.
D458,996 S 6/2002 Bryant et al.
6,423,064 B1 7/2002 Kluger
6,440,131 B1 8/2002 Haidukewych
6,440,135 B2 8/2002 Orbay et al.
D463,557 S 9/2002 Bryant et al.
D463,558 S 9/2002 Bryant et al.
D463,559 S 9/2002 Bryant et al.
6,454,769 B2 9/2002 Wagner et al.
6,454,770 B1 9/2002 Klaue
D464,136 S 10/2002 Bryant et al.
D464,731 S 10/2002 Bryant et al.
6,468,278 B1 10/2002 Mueckter
6,488,685 B1 12/2002 Manderson
D469,532 S 1/2003 Bryant et al.
D469,533 S 1/2003 Bryant et al.
D469,534 S 1/2003 Bryant et al.
6,503,252 B2 1/2003 Hansson
6,503,281 B1 1/2003 Mallory
6,508,819 B1 1/2003 Orbay
D469,874 S 2/2003 Bryant et al.
D469,875 S 2/2003 Bryant et al.
D470,588 S 2/2003 Bryant et al.
6,525,525 B1 2/2003 Azinger
6,527,776 B1 3/2003 Michelson
6,533,789 B1 3/2003 Hall et al.
6,565,525 B1 5/2003 Burbank et al.
6,565,569 B1 5/2003 Assaker et al.
6,575,975 B2 6/2003 Brace et al.
6,602,256 B1 8/2003 Hayes
6,605,090 B1 8/2003 Trieu et al.
D479,331 S 9/2003 Pike et al.
D480,141 S 9/2003 Benirschke et al.
6,623,486 B1 9/2003 Weaver et al.
6,648,891 B2 11/2003 Kim
6,666,868 B2 12/2003 Fallin

(56) References Cited

U.S. PATENT DOCUMENTS 6,669,700 B1 12/2003 Farris et al.
6,669,701 B2 12/2003 Steiner et al.
6,712,820 B2 3/2004 Orbay
6,719,759 B2 4/2004 Wagner et al.
6,730,091 B1 5/2004 Pfefferle et al.
6,767,351 B2 7/2004 Orbay et al.
6,835,197 B2 12/2004 Roth et al.
6,863,483 B2 * 3/2005 Koenig ..... F16B 39/30 411/309
6,866,665 B2 3/2005 Orbay
6,875,215 B2 4/2005 Taras et al.
6,893,443 B2 5/2005 Frigg et al.
6,955,677 B2 10/2005 Dahners
6,974,461 B1 12/2005 Wolter
7,001,388 B2 2/2006 Orbay et al.
7,044,953 B2 5/2006 Capanni
7,128,744 B2 10/2006 Weaver et al.
7,169,149 B1 1/2007 Hajianpour
7,179,260 B2 2/2007 Gerlach et al.
7,229,445 B2 6/2007 Hayeck et al.
7,282,053 B2 10/2007 Orbay
7,294,130 B2 11/2007 Orbay
7,309,340 B2 12/2007 Fallin et al.
7,316,687 B2 1/2008 Aikins et al.
7,338,491 B2 3/2008 Baker et al.
7,341,589 B2 3/2008 Weaver et al.
7,354,441 B2 4/2008 Frigg
7,517,350 B2 4/2009 Weiner et al.
7,527,639 B2 5/2009 Orbay et al.
7,537,596 B2 5/2009 Jensen
7,635,381 B2 12/2009 Orbay
7,637,928 B2 12/2009 Fernandez
7,641,677 B2 1/2010 Weiner et al.
7,695,472 B2 4/2010 Young
7,695,502 B2 4/2010 Orbay et al.
7,766,916 B2 8/2010 Leyden et al.
7,771,433 B2 8/2010 Orbay et al.
7,771,457 B2 8/2010 Kay et al.
7,776,076 B2 8/2010 Grady
7,776,916 B2 8/2010 Freeman et al.
7,857,838 B2 12/2010 Orbay
7,867,260 B2 1/2011 Meyer et al.
7,905,909 B2 3/2011 Orbay et al.
7,951,176 B2 5/2011 Grady et al.
8,075,561 B2 12/2011 Wolter
8,092,505 B2 1/2012 Sommers
8,118,846 B2 2/2012 Leither et al.
8,118,848 B2 2/2012 Ducharme et al.
8,337,535 B2 12/2012 White et al.
8,343,196 B2 1/2013 Schneider
8,403,967 B2 3/2013 Orbay
8,506,607 B2 8/2013 Eckhof et al.
8,518,042 B2 8/2013 Winslow et al.
8,556,945 B2 10/2013 Orbay
8,574,268 B2 11/2013 Chan et al.
8,579,946 B2 11/2013 Orbay
8,641,744 B2 2/2014 Weaver et al.
8,758,346 B2 6/2014 Koay et al.
8,814,918 B2 8/2014 Orbay et al.
8,845,698 B2 9/2014 Schneider
8,852,245 B2 10/2014 Schneider
8,876,873 B2 11/2014 Schneider
8,894,693 B2 11/2014 Petit et al.
8,940,029 B2 1/2015 Leung et al.
9,072,558 B2 7/2015 Orbay
9,101,423 B2 8/2015 Hulliger
9,107,711 B2 8/2015 Hainard
9,168,075 B2 10/2015 Dell Oca
9,265,542 B2 2/2016 Koay et al.
9,277,947 B2 3/2016 Koay et al.
9,295,505 B2 3/2016 Schneider
9,308,034 B2 4/2016 Grady
9,314,284 B2 4/2016 Chan et al.
9,387,022 B2 7/2016 Koay et al. ..... A61B 17/866
9,433,454 B2 9/2016 Paolino et al.
9,492,212 B2 11/2016 Ahrens et al.
9,498,267 B2 11/2016 Pfeiffer et al.
9,510,880 B2 12/2016 Terrill et al.
9,554,909 B2 1/2017 Donner et al.
9,603,641 B2 3/2017 Hulliger
9,855,083 B2 1/2018 Mighell et al.
9,867,643 B2 1/2018 Terrill et al.
9,931,148 B2 4/2018 Grady
10,342,586 B2 7/2019 Schneider
10,624,686 B2 4/2020 Lopez et al.
10,772,665 B2 * 9/2020 Bosshard ..... A61B 17/8052
11,026,723 B2 * 6/2021 Rezach ..... B33Y 80/00
11,026,727 B2 * 6/2021 Bosshard ..... A61B 17/86
2001/0000186 A1 4/2001 Bramlet et al.
2001/0011172 A1 8/2001 Orbay et al.
2001/0012940 A1 8/2001 Tunc
2002/0009889 A1 1/2002 Sakai
2002/0013587 A1 1/2002 Winquist et al.
2002/0032446 A1 3/2002 Orbay
2002/0045901 A1 4/2002 Wagner et al.
2002/0049445 A1 4/2002 Hall et al.
2002/0062127 A1 5/2002 Schumacher et al.
2002/0065516 A1 5/2002 Winquist et al.
2002/0128654 A1 9/2002 Steger et al.
2002/0143337 A1 10/2002 Orbay et al.
2002/0143338 A1 10/2002 Orbay et al.
2002/0156474 A1 10/2002 Wack et al.
2002/0183752 A1 12/2002 Steiner et al.
2002/0183753 A1 12/2002 Manderson
2003/0040748 A1 2/2003 Aikins et al.
2003/0055435 A1 3/2003 Barrick
2003/0060827 A1 3/2003 Coughln
2003/0083660 A1 5/2003 Orbay
2003/0083661 A1 5/2003 Orbay et al.
2003/0105461 A1 6/2003 Putnam
2003/0125738 A1 7/2003 Khanna
2003/0135212 A1 7/2003 Y Chow
2003/0135216 A1 7/2003 Sevrain
2004/0030339 A1 2/2004 Wack et al.
2004/0049193 A1 3/2004 Capanni
2004/0059334 A1 3/2004 Weaver et al.
2004/0059335 A1 3/2004 Weaver et al.
2004/0073218 A1 4/2004 Dahners
2004/0097937 A1 5/2004 Pike et al.
2004/0097941 A1 5/2004 Weiner et al.
2004/0111089 A1 6/2004 Stevens et al.
2004/0215198 A1 10/2004 Marnay et al.
2004/0254579 A1 12/2004 Buhren et al.
2004/0260291 A1 12/2004 Jensen
2004/0260306 A1 12/2004 Fallin et al.
2005/0015089 A1 1/2005 Young et al.
2005/0049593 A1 3/2005 Duong et al.
2005/0080421 A1 4/2005 Weaver et al.
2005/0085818 A1 4/2005 Huebner
2005/0107796 A1 5/2005 Gerlach et al.
2005/0165400 A1 7/2005 Fernandez
2005/0171544 A1 8/2005 Falkner, Jr.
2005/0187555 A1 8/2005 Biedermann et al.
2005/0216001 A1 9/2005 David
2005/0261688 A1 11/2005 Grady et al.
2005/0277937 A1 12/2005 Leung et al.
2006/0004361 A1 1/2006 Hayeck et al.
2006/0009771 A1 * 1/2006 Orbay ..... A61B 17/8605 606/291
2006/0058797 A1 3/2006 Mathieu et al.
2006/0200151 A1 9/2006 Ducharme et al.
2006/0217722 A1 9/2006 Dutoit et al.
2006/0235400 A1 10/2006 Schneider
2006/0264946 A1 11/2006 Young
2007/0016205 A1 1/2007 Beutter et al.
2007/0083207 A1 4/2007 Ziolo et al.
2007/0088360 A1 4/2007 Orbay et al.
2007/0162016 A1 7/2007 Matityahu
2007/0206244 A1 9/2007 Kobayashi
2007/0208378 A1 9/2007 Bonutti et al.
2007/0225716 A1 9/2007 Deffenbaugh et al.
2007/0276386 A1 11/2007 Gerlach et al.
2007/0276402 A1 11/2007 Frankel et al.
2008/0065070 A1 3/2008 Freid et al.

(56) References Cited

U.S. PATENT DOCUMENTS

2008/0132960 A1 6/2008 Weaver et al.
2008/0140130 A1* 6/2008 Chan ..... A61B 17/8605 606/280
2008/0208259 A1 8/2008 Gilbert et al.
2008/0234749 A1 9/2008 Forstein
2008/0234752 A1* 9/2008 Dahners ..... A61B 17/8869 606/291
2008/0300637 A1 12/2008 Austin et al.
2009/0018557 A1 1/2009 Pisharodi
2009/0018588 A1 1/2009 Eckhof et al.
2009/0024172 A1 1/2009 Pizzicara
2009/0036933 A1 2/2009 Dube et al.
2009/0076553 A1 3/2009 Wolter
2009/0076554 A1 3/2009 Huebner et al.
2009/0099610 A1 4/2009 Johnson et al.
2009/0118768 A1 5/2009 Sixto et al.
2009/0143824 A1 6/2009 Austin et al.
2009/0143825 A1 6/2009 Graham et al.
2009/0216242 A1 8/2009 Riemer et al.
2009/0281543 A1 11/2009 Orbay et al.
2009/0287258 A1 11/2009 Vannemreddy
2009/0292318 A1 11/2009 White et al.
2009/0312803 A1 12/2009 Austin et al.
2010/0016858 A1 1/2010 Michel
2010/0030277 A1 2/2010 Haidukewych et al.
2010/0057086 A1 3/2010 Price et al.
2010/0076496 A1 3/2010 Fernandez
2010/0094357 A1 4/2010 Wallenstein et al.
2010/0100134 A1 4/2010 Mocanu
2010/0137919 A1 6/2010 Wolter
2010/0274296 A1 10/2010 Appenzeller et al.
2010/0312285 A1 12/2010 White et al.
2010/0312286 A1* 12/2010 Dell'Oca ..... A61B 17/8057 606/291
2011/0046681 A1 2/2011 Prandi et al.
2011/0087229 A1 4/2011 Kubiak et al.
2011/0106081 A1 5/2011 Graham et al.
2011/0184471 A1 7/2011 Foley et al.
2011/0224671 A1 9/2011 Koay et al.
2011/0224736 A1 9/2011 Humphrey
2011/0264149 A1 10/2011 Pappalardo et al.
2011/0301608 A1 12/2011 Roth et al.
2012/0123484 A1 5/2012 Lietz et al.
2012/0143193 A1 6/2012 Hulliger
2012/0197307 A1 8/2012 Fritzinger et al.
2012/0245642 A1 9/2012 Giannoudis et al.
2013/0096631 A1 4/2013 Leung et al.
2013/0116735 A1 5/2013 Schneider
2013/0172943 A1 7/2013 Austin et al.
2013/0190828 A1 7/2013 Schneider
2013/0190829 A1 7/2013 Batsch et al.
2013/0197589 A1 8/2013 Schneider
2013/0245699 A1 9/2013 Orbay et al.
2013/0261675 A1 10/2013 Fritzinger
2014/0005728 A1 1/2014 Koay et al.
2014/0018862 A1 1/2014 Koay et al.
2014/0058455 A1 2/2014 Appenzeller et al.
2014/0066998 A1 3/2014 Martin
2014/0180345 A1 6/2014 Chan et al.
2014/0207194 A1 7/2014 Wolter
2014/0222084 A1 8/2014 Fritzinger et al.
2014/0236154 A1 8/2014 Liao et al.
2014/0271028 A1 9/2014 Arnett
2014/0277161 A1 9/2014 Spratt et al.
2014/0277180 A1 9/2014 Paolino et al.
2014/0316473 A1 10/2014 Pfeiffer et al.
2014/0324108 A1 10/2014 Orbay et al.
2015/0018829 A1 1/2015 Woodburn et al.
2015/0051651 A1 2/2015 Terrill et al.
2015/0105829 A1 4/2015 Laird
2015/0250485 A1 9/2015 Niederberger et al.
2015/0257802 A1 9/2015 Wolf et al.
2015/0327897 A1 11/2015 Hulliger
2015/0327898 A1 11/2015 Martin
2015/0359575 A1 12/2015 Pech et al.
2016/0074081 A1 3/2016 Weaver et al.
2016/0089191 A1 3/2016 Pak et al.
2016/0143676 A1 5/2016 Koay et al.
2016/0166294 A1 6/2016 Schneider
2016/0242829 A1 8/2016 Kim et al.
2016/0278826 A1 9/2016 Epperly
2016/0310184 A1 10/2016 Kazanovicz et al.
2016/0317205 A1 11/2016 Baker
2016/0367299 A1 12/2016 Paolino et al.
2017/0086891 A1 3/2017 Wolf et al.
2017/0265915 A1 9/2017 Langdale et al.
2017/0319248 A1 11/2017 Milella et al.
2018/0008326 A1 1/2018 Hulliger et al.
2018/0021072 A1 1/2018 Roth
2018/0036049 A1 2/2018 Kobayashi
2018/0064476 A1 3/2018 Lopez et al.
2018/0064477 A1 3/2018 Lopez et al.
2018/0064479 A1 3/2018 Lopez et al.
2018/0132913 A1 5/2018 Davison et al.
2018/0235681 A1 8/2018 Chambers et al.
2019/0290338 A1* 9/2019 Bosshard ..... A61B 17/8047
2019/0298426 A1 10/2019 Bosshard et al.
2020/0214749 A1 7/2020 Lopez et al.

FOREIGN PATENT DOCUMENTS

CA 2047521 1/1992
CA 2047521 A1 1/1992
CA 2536960 A1 3/2005
CA 2920883 A1 2/2015
CH 611147 A5 5/1979
CH 670755 A5 7/1989
CH 672245 A5 11/1989
CH 675531 A5 10/1990
CN 1486162 A 3/2004
CN 1764418 A 4/2006
CN 1819799 A 8/2006
CN 101272743 A 9/2008
CN 101355911 A 1/2009
CN 101505670 A 8/2009
CN 101600398 A 12/2009
CN 101778604 A 7/2010
CN 101842057 A 9/2010
CN 102497830 A 6/2012
CN 102791211 11/2012
CN 103068329 A 4/2013
CN 103417281 A 12/2013
CN 103889350 6/2014
CN 203970523 U 12/2014
CN 104287820 A 1/2015
CN 104684494 A 6/2015
CN 105517501 A 4/2016
DE 2933637 A1 4/1980
DE 3442004 C1 4/1986
DE 3722852 A1 1/1989
DE 3743638 A1 7/1989
DE 4004941 A1 7/1989
DE 3942326 A1 6/1991
DE 4201531 A1 7/1993
DE 4341980 A1 6/1995
DE 4343117 A1 6/1995
DE 4438264 A1 3/1996
DE 19636733 A1 4/1997
DE 19629011 A1 1/1998
DE 9321544 U1 9/1999
DE 19832513 A1 2/2000
DE 19858889 A1 6/2000
DE 10015734 A1 9/2001
DE 10125092 A1 12/2001
DE 20309361 U1 9/2003
DE 20317651 U1 3/2004
DE 10319781 B3 8/2004
DE 102004009429 A1 9/2005
DE 102005042766 A1 1/2007
DE 202006019220 U1 1/2007
DE 202008000914 U1 5/2007
DE 202007017159 U1 5/2008
DE 102010048052 4/2012
DE 102016112845 A1 1/2018

(56) References Cited

FOREIGN PATENT DOCUMENTS

| | | | |
|---|---|---|---|
| DE | 202014011161 | U1 | 3/2018 |
| EP | 0053999 | A1 | 6/1982 |
| EP | 0158030 | A1 | 10/1985 |
| EP | 0180532 | A1 | 5/1986 |
| EP | 0207884 | A2 | 1/1987 |
| EP | 0241914 | A2 | 10/1987 |
| EP | 0244782 | A1 | 11/1987 |
| EP | 0251583 | A2 | 1/1988 |
| EP | 0266146 | A2 | 5/1988 |
| EP | 0274713 | A1 | 7/1988 |
| EP | 0290138 | A2 | 11/1988 |
| EP | 0291632 | A1 | 11/1988 |
| EP | 0299160 | A1 | 1/1989 |
| EP | 0337288 | A1 | 10/1989 |
| EP | 0360139 | A2 | 3/1990 |
| EP | 0381462 | A2 | 8/1990 |
| EP | 0382256 | A1 | 8/1990 |
| EP | 0410309 | A1 | 1/1991 |
| EP | 0436885 | A2 | 7/1991 |
| EP | 0471418 | A1 | 2/1992 |
| EP | 0506420 | A1 | 9/1992 |
| EP | 0515828 | A1 | 12/1992 |
| EP | 0530585 | A2 | 3/1993 |
| EP | 0532421 | A1 | 3/1993 |
| EP | 0546460 | A1 | 6/1993 |
| EP | 0649635 | A1 | 4/1995 |
| EP | 0668059 | A1 | 8/1995 |
| EP | 0760231 | A1 | 3/1997 |
| EP | 0848600 | A1 | 6/1998 |
| EP | 0988833 | A2 | 3/2000 |
| EP | 1132052 | A2 | 9/2001 |
| EP | 1468655 | A2 | 10/2004 |
| EP | 1568329 | A1 | 8/2005 |
| EP | 1604619 | A1 | 12/2005 |
| EP | 1658015 | A1 | 5/2006 |
| EP | 1712197 | A1 | 10/2006 |
| EP | 1741397 | A2 | 1/2007 |
| EP | 1764052 | A1 | 3/2007 |
| EP | 1764552 | A1 | 3/2007 |
| EP | 1767160 | A2 | 3/2007 |
| EP | 1878394 | A2 | 1/2008 |
| EP | 2248479 | A1 | 11/2010 |
| EP | 2529685 | A1 | 12/2012 |
| FR | 2233973 | A1 | 1/1975 |
| FR | 2405062 | A1 | 5/1979 |
| FR | 2405705 | A1 | 5/1979 |
| FR | 2405706 | A1 | 5/1979 |
| FR | 2496429 | A3 | 6/1982 |
| FR | 2606268 | A1 | 5/1988 |
| FR | 2622431 | A1 | 5/1989 |
| FR | 2650500 | A1 | 2/1991 |
| FR | 2671966 | A3 | 7/1992 |
| FR | 2674118 | A1 | 9/1992 |
| FR | 2677876 | A1 | 12/1992 |
| FR | 0742618 | A | 3/1993 |
| FR | 2706763 | A1 | 12/1994 |
| FR | 2739151 | A1 | 3/1997 |
| FR | 2757370 | A1 | 6/1998 |
| FR | 2802082 | A1 | 6/2001 |
| GB | 0997733 | A | 7/1965 |
| GB | 1237405 | A | 6/1971 |
| GB | 1250413 | A | 10/1971 |
| GB | 1312189 | A | 4/1973 |
| GB | 1385398 | A | 2/1975 |
| GB | 2017502 | A | 10/1979 |
| GB | 1575194 | A | 9/1980 |
| GB | 2090745 | A | 7/1982 |
| GB | 2245498 | A | 1/1992 |
| GB | 2257913 | A | 1/1993 |
| JP | 02-121652 | A | 5/1990 |
| JP | 03-058150 | | 3/1991 |
| JP | 03-158150 | | 7/1991 |
| JP | 04-138152 | A | 5/1992 |
| JP | 06-045941 | | 2/1994 |
| JP | 06-125918 | | 5/1994 |
| JP | 06-245941 | | 9/1994 |
| JP | 08-098846 | | 4/1996 |
| JP | 08-126650 | | 5/1996 |
| JP | 08-257034 | | 10/1996 |
| JP | 08-266562 | A | 10/1996 |
| JP | 09-108237 | | 4/1997 |
| JP | 10-118096 | A | 5/1998 |
| JP | 11-076259 | | 3/1999 |
| JP | 11-299804 | | 8/1999 |
| JP | 11-276501 | | 10/1999 |
| JP | 11-512004 | | 10/1999 |
| JP | 11-318930 | | 11/1999 |
| JP | 2000-000247 | A | 1/2000 |
| JP | 2000-152944 | A | 6/2000 |
| JP | 2001-149379 | A | 6/2001 |
| JP | 2001-161704 | A | 6/2001 |
| JP | 2001-514039 | | 9/2001 |
| JP | 2001-525701 | | 12/2001 |
| JP | 2001-525702 | | 12/2001 |
| JP | 2002-095673 | A | 4/2002 |
| JP | 2002-232185 | A | 8/2002 |
| JP | 2002-532185 | A | 10/2002 |
| JP | 2002-345836 | A | 12/2002 |
| JP | 2002-542875 | | 12/2002 |
| JP | 2003-024344 | A | 1/2003 |
| JP | 2003-038508 | A | 2/2003 |
| JP | 2003-038509 | A | 2/2003 |
| JP | 2003-509107 | | 3/2003 |
| JP | 2003-521303 | | 7/2003 |
| JP | 2010-536427 | A | 12/2010 |
| JP | 2011-529346 | A | 12/2011 |
| JP | 2013-528075 | A | 7/2013 |
| JP | 2015-525616 | A | 9/2015 |
| JP | 2016-512711 | A | 5/2016 |
| JP | 2017-507739 | A | 3/2017 |
| KR | 10-2007-0034449 | A | 3/2007 |
| KR | 10-2008-0028917 | A | 4/2008 |
| SU | 1037911 | | 8/1983 |
| SU | 1279626 | | 12/1986 |
| WO | 87/00419 | A1 | 1/1987 |
| WO | 87/06982 | A1 | 11/1987 |
| WO | 88/03781 | A1 | 6/1988 |
| WO | 92/11819 | A1 | 7/1992 |
| WO | 93/11714 | A1 | 6/1993 |
| WO | 93/15678 | A1 | 8/1993 |
| WO | 93/22982 | A1 | 11/1993 |
| WO | 94/02073 | A1 | 2/1994 |
| WO | 95/32674 | A1 | 12/1995 |
| WO | 96/17556 | A1 | 6/1996 |
| WO | 96/25892 | A1 | 8/1996 |
| WO | 96/29948 | A1 | 10/1996 |
| WO | 97/08999 | A1 | 3/1997 |
| WO | 97/09000 | A1 | 3/1997 |
| WO | 97/20514 | A1 | 6/1997 |
| WO | 98/02105 | A1 | 1/1998 |
| WO | 98/05263 | A1 | 2/1998 |
| WO | 98/51226 | A2 | 11/1998 |
| WO | 98/51368 | A1 | 11/1998 |
| WO | 99/25266 | A1 | 5/1999 |
| WO | 99/44529 | A1 | 9/1999 |
| WO | 00/53110 | A1 | 9/2000 |
| WO | 00/53111 | A1 | 9/2000 |
| WO | 00/66012 | A1 | 11/2000 |
| WO | 01/19267 | A1 | 3/2001 |
| WO | 01/19268 | A1 | 3/2001 |
| WO | 01/26566 | | 4/2001 |
| WO | 01/54601 | A1 | 8/2001 |
| WO | 01/89400 | A2 | 11/2001 |
| WO | 02/71963 | | 9/2002 |
| WO | 02/96309 | A1 | 12/2002 |
| WO | 03/02856 | | 1/2003 |
| WO | 03/22166 | | 3/2003 |
| WO | 03/28567 | | 4/2003 |
| WO | 03/57055 | A1 | 7/2003 |
| WO | 2004/043277 | A1 | 5/2004 |
| WO | 2004/089233 | A1 | 10/2004 |
| WO | 2004/107957 | A2 | 12/2004 |
| WO | 2005/018472 | A1 | 3/2005 |
| WO | 2005/044121 | A1 | 5/2005 |

(56) References Cited

FOREIGN PATENT DOCUMENTS

| | | | |
|---|---|---|---|
| WO | 2007/014279 | A2 | 2/2007 |
| WO | 2007/108734 | A1 | 9/2007 |
| WO | 2009/023666 | A2 | 2/2009 |
| WO | 2009/058969 | A1 | 5/2009 |
| WO | 2011/032140 | A1 | 3/2011 |
| WO | 2012/112327 | A2 | 8/2012 |
| WO | 2013/045713 | A1 | 4/2013 |
| WO | 2015/138303 | | 9/2015 |
| WO | 2017/048909 | A1 | 3/2017 |
| WO | 2018/048667 | A1 | 3/2018 |
| WO | 2018/048668 | A1 | 3/2018 |

OTHER PUBLICATIONS

Bone Fixation Method, U.S. Appl. No. 09/848,251, filed May 4, 2001.
Bone Plating System, U.S. Appl. No. 09/660,287, filed Sep. 12, 2000.
Zimmer Advertisement, J. of Orthopaedic Trauma, vol. 12, No. 5, Jun./Jul. 1998.
Vattolo, M., Thesis, "The Effect of Grooves in Osteosynthesis Plates on the Restructuring of the Corticalis," Laboratory for Experimental Surgery, Swiss Research Institute, 1986 (original in German, translation to English attached with Certification).
U.S. Appl. No. 15/940,761, Locking Structures for Affixing Bone Anchors to a Bone Plate, and Related Systems and Methods, Mar. 29, 2018.
U.S. Appl. No. 15/926,390, Bone Plate With Form-Fitting Variable-Angle Locking Hole, filed Mar. 20, 2018.
Update, Titanium LC-DCP Condylar Buttress Plate, Jun. 15, 1995 (Synthes) ("The LC-DCP update").
Universelle Rekonstruktionsplatte URP 2 4-3.2 (UniRecon-Registered), Swiss Dent, 17,1996, pp. 19-25.
The Titanium Distal Radius Plate Technique Guide, published by Synthes, 1997.
The Titanium Distal Radius Plate Technique Guide, (the "DRP Guide") published by Synthes in 1996.
The Locking Reconstruction Plate Technique Guide, published by Synthes, 1997.
The Distal Radius Plate Instrument and Implant Set Technique Guide, (Synthes) ("1999 Radius Plate Guide").
The Distal Radius Plate Instrument and Implant Set Technique Guide, (Synthes) ("1998 Radius Plate Guide").
Technique Guide: 2.4 mm Variable Angle LCP Distal Radius System. Synthes, 2008,43 pages.
Technique Guide, Less Invasive Stabilization (LISS), Oct. 2003.
Synthes' Supporting Memorandum for Reconsideration of Claim Construction (without supporting Declaration) in the Pennsylvania Action, dated Feb. 19, 2008.
Synthes' Summary Judgment Motion of No Invalidity Based on K982222 Summary including supporting memorandum, and declarations of A. Silversti and B. Liu (with supporting exhibits), dated Sep. 10, 2008.
Synthes' Responsive Claim Construction Brief (without exhibits) for the Pennsylvania Action, dated Apr. 20, 2007.
Synthes' Response to Smith & Nephew's Statement of Facts in Support of Smith & Nephew's Motion for Summary Judgment of Invalidity of the '744 patent; dated Sep. 29, 2008; 19 pages.
Synthes' Response to Motion for Leave to Amend Answer, Civil Action No. 03-0084 (E.D. Pa.), dated Aug. 9, 2007.
Synthes' Reply to Smith & Nephew's Opposition to Synthes Motion for Reconsideration of Claim Construction for the '486 patent in the Pennsylvania Action, dated Mar. 14, 2008.
Synthes' Opposition to Smith & Nephew's Motion for Summary Judgment of Invalidity of the '744 patent; dated Sep. 29, 2008; 22 pages.
Synthes' Opening Claim Construction Brief (without supporting declaration and attached exhibits but including Appendix A & B) for the Pennsylvania Action, dated Mar. 16, 2007 (Dkt. 54) (Ex. 5).
Synthes' 1996 Titanium Modular Hand System brochure (the "Hand System Brochure") [SNI-0290287-294] (Ex. 47).
Synthes Titanium Modular Hand System, 1996.
Synthes Opposition to Smith & Nephew's Motion for Summary Judgment of Invalidity of Claims 10-12 of the '486 Patent, dated Sep. 29, 2008 (Dkt. 159) (Ex 67).
Synthes 1997 Catalog, published by Synthes, Mar. 1997; part 2, 261 pgs.
Synthes 1997 Catalog, published by Synthes, Mar. 1997; part 1, 200 pgs.
Sutter, F., et al., "Titanplasma-beschichtetes Hohlschrauben—und Rekonstructions-platten—System (THRP) zur Oberbriickung van Kieferdefekten," Chirurg No. 55, pp. 741-748,1984 [SNI-0006164-171], and translation thereof [SNI-0006152-163] (Ex. 33).
Surgical Instruments Catalog, Collin & Co., 1935 (original in French, translation to English of pp. 392-397 attached with certification).
Supplemental Expert Report of Clifford FI. Turen, M.D., May 2009 (with Exhibit 1), dated Aug. 8, 2008(Ex.60).
Supplement to Apr. 9, 2008 Expert Report of John F. Witherspoon (without exhibits), dated May 14, 2008 (Ex. 74).
Supplement to Apr. 9, 2008 Expert Report of J. Lawrence Marsh in the Pennsylvania Action (with Exhibit 1), dated May 14, 2008 (Ex. 46).
Summary of Safety and Effectiveness Information [510(k) Summary], K982222, Jul. 29, 1998.
Stryker, "VariAx Distal Radius: Locking Plate System", wwvv.osteosynthesis.stryker.com, 2006, 12 pages.
Stay Order in Pennsylvania Action, dated Jul. 13, 2009.
Smith and Nephew's Opposition to Synthes Motion for Summary Judgment of No Invalidity Based on K982222(including Opposition Memorandum, Statement of Undisputed Facts, K. Doyle Declaration with Exhibits A-F and R. King's Declaration with Exhibits A-D), dated Sep. 29, 2008( Dkt. 154) (Ex. 63).
Smith & Newphew Statement of Undisputed Facts in Support of its Motion for Summary Judgment of Invalidity of U.S. Pat. No. 7,128,744; dated Sep. 29, 2008; 8 pages.
*Smith & Nephew, Inc.* v. *Rea*, Federal Circuit Opinion dated Jul. 9, 2013, 18 pages.
Smith & Nephew's Third Supplemental Response to Interrogatories Nos. 4, 5, 6, 8 and 9; Second Supplemental Responses to Interrogatories Nos. 1,2, 3,10,11 and 12; and First Supplemental Responses to Interrogatories Nos. 13,15 and 17 (with Smith & Nephew Exhibit 1 thereto), dated Aug. 11, 2008 (Ex. 14).
Smith & Nephew's Responsive Claim Construction Brief (without exhibits) for the Pennsylvania Action, dated Apr. 20, 2007 (Dkt. 60) (Ex. 8).
Smith & Nephew's Responses and Objections to Plaintiffs Fourth Set of Interrogatories Nos. 15-16, dated May 21, 2008 (Ex. 55).
Smith & Nephew's Opposition to Synthes' Motion for Reconsideration of Claim Construction for the '486 Patent in the Pennsylvania Action, dated Mar. 4, 2008 (Dkt. 108) (Ex. 11).
Smith & Nephew's Opening Claim Construction Brief (without exhibits) for the Pennsylvania Action, dated Mar. 16, 2007 (Dkt. 53) (Ex. 6).
Smith & Nephew's Memorandum in Support of Motion for Leave to file Amended Answer in the Pennsylvania Action, dated Aug. 7, 2007 (Dkt. 77) (Ex. 70).
Smith & Nephew's Memorandum in Support of its Motion for Summary Judgment of Invalidly of U.S. Pat. No. 7,128,744; dated Sep. 10, 2008; 22 pages.
Smith & Nephew's Memorandum in Support of its Motion for Partial Summary Judgment of Invalidity of Claims 10-12 of the '486 patent, dated Sep. 10, 2008.
Smith & Nephew's Amended Answer in the Pennsylvania Action (without Exhibits A-S ) in the Pennsylvania Action, dated Aug. 7, 2007.
Smith & Nephew Amended Answer and Counterclaims of Defendant, Civil Action No. 03-0084 (E.D. Pa.), dated Aug. 7, 2007.
Second Supplement to Apr. 9, 2008 Expert Report of J. Lawrence Marsh (with Exhibit 1), dated Sep. 3, 2008.
Second Supplement to Apr. 9, 2008 Expert Report of David Seligson, M.D., dated Sep. 3, 2008.
Schuhli Technique Guide, published by Synthes, 1995.

(56) References Cited

OTHER PUBLICATIONS

European Patent Application No. 12006617.0: Extended European Search Report dated Jan. 21, 2013, 8 pages.
European Patent Application No. 12006615.4: Extended European Search Report dated Jan. 21, 2013, 7 pages.
European Patent Application No. 12006606.3: Extended European Search Report dated Jan. 21, 2013, 7 pages.
English translation of International Patent Application No. PCT/CH03/00577: International Search Report dated Apr. 28, 2004, 4 pages.
Dr. Turen's Aug. 15, 2008 deposition transcript in the Pennsylvania Action (Ex. 61).
Dr. Parsons Aug. 7, 2008 deposition transcript in the Pennsylvania Action (Ex. 58).
Dr. Marsh's Jul. 26,2008 Deposition transcript in the Pennsylvania Action (Ex. 52).
Docket sheet for the Pennsylvania Action-2:03-cv-0084 (CDJ) (Ex. 4) filed Jan. 7, 2003.
Docket sheet for the California Action-3:07-cv-00309-L-AJB (Ex. 1) Filed Feb. 14, 2007.
Defendant's Motion for Leave to Amend Answer to Assert Allegations of Inequitable Conduct, Civil Action No. 03-0084 (E.D. Pa.), dated Aug. 7, 2007.
Declaration of Robert A. King in Support of their Motion for Partial Summary Judgment of Invalidity of Claims 10-12 of U.S. Pat. No. 6,623,486 (without exhibits), dated Sep. 10, 2008.
Declaration of J. Russell Parsons, Ph.D. in Support of Synthes Opposition to Smith & Nephew's Motion for Summary Judgement of Invalidity of the '744 patent (w/o Exhibits 1-4) dated Sep. 29, 2008; 15 pages.
Declaration of J. Russell Parsons, Ph.D. in Support of Synthes Opposition to Smith & Nephew's Motion for Partial Summary Judgment of Invalidity of Method Claims 10-12 of U.S. Pat. No. 6,623,486 (with Exhibits 1-4), dated Sep. 29, 2008 (Dkt. 160) (Ex. 68).
Declaration of J. Lawrence Marsh, M.D. dated Nov. 22, 2010.
Declaration of J. Lawrence Marsh, M.D. dated Jun. 25, 2010.
Declaration of J. Lawrence Marsh, M.D. dated Jun. 3, 2010.
Declaration of Dr. Seligson in Support of Smith & Nephew's Motion for Partial Summary 175 Judgment of Invalidity of Claims 10-12 of U.S. Pat. No. 6,623,486 dated Sep. 9, 2008 (with Exhibit 1, pp. 16-66 dated Sep. 10, 2008).
Declaration of Clifford H. Turen, M.D. in Support of Synthes' Opposition to Smith & Nephew's Motion for Partial Summary Judgment of Invalidity of Method Claims 10-12 of U.S. Pat. No. 6,623,486 (with Exhibits 1-4 ), dated Sep. 29, 2008.
Declaration of Charles E. Van Horn, Esq., in Support of Synthes Opposition to Smith & Nephew's Motion for Summary Judgement of Invalidity of the '744 patent (w/o Exhibits 1-6) dated Sep. 29, 2008; 12 pages.
Court Order denying Synthes' Motion for Reconsideration of Claim Construction for the '486 Patent in the Pennsylvania Action, dated Jun. 30, 2008.
Collins Instruments de Chirurgie, published 1935, as illustrated at http://www.litos.com/pages/winkelstabilitaet e.html (Sep. 26, 2007) ("Collin Catalog") [SNI-0258552-556] (Ex. 20).
Claim Construction Order in Pennsylvania Action, dated Feb. 4, 2008.
Brief in Support of Defendants' Motion for Leave to Amend Answer to Assert Allegations of Inequitable Conduct, Civil Action No. 03-0084 (E.D. Pa.), dated Aug. 7, 2007.
Bone Plating System, U.S. Appl. No. 09/660,287.
Bone Fixation Method, U.S. Appl. No. 09/848,251.
Bolhofner, et al., The Results of Open Reduction and Internal Fixation of Distal Femur Fractures Using a Biologic (Indirect) Reduction Technique; Journal of Orthopedic Trauma, vol. 10, No. 6, pp. 372-377, Liooincort-Raven Publishers, Copyright 1996.
AO/ASIF Instruments and Implants, A Technical Manual, Springer-Verlag, 1994 (the "AO-ASIF Manual").
Answer to Amended Complaint and Counterclaims, Civil Action No. 03-0084 (E .. D. Pa), filed Dec. 5. 2006.
Amended Complaint for Patent Infringement, Civil Action No. 03-0084 (E.D. Pa.), filed Nov. 13, 2006.
ACE SymmetryTM, "Curves in All the Right Places", 1996, 3 pages.
ACE Symmetry Trademark Titanium Upper Extremity Plates, ACE Medical Company, 1996, 2 pages.
ACE Symmetry (Trademark), "Curves in All the Right Places", Titanium Upper Extremity Plates, Ace Medical Company, 1996, 6 pages.
510(k) Summary for Synthes (USA)'s Distal Femur Plate (DFP) System (K982222), dated Jul. 29, 1998 (attached as Exhibit 0 to Amended Answer).
510(k) Summary for Synthes (USA)'s Anatomical Locking Plate System (K961413), dated Aug. 7, 1996 (attached as Exhibit Q to Amended Answer).
510(k) Summary for Synthes (USA)'s 2.4 mm Universal Locking Plate System (K961421 ), dated Jun. 26, 1996 (attached as Exhibit S to Amended Answer).
510(k) Disclosure K982732, Oct. 8, 1998 (Synthes) ("K982732") [SNI-0259741-744] (Ex. 39).
510(k) Disclosure K963798, Nov. 27, 1996 (Synthes) ("K963798") [SNI-0258398] (Ex. 38).
510(k) Disclosure K962616, Sep. 3, 1996 (Synthes) ("K962616") [SNI-0258397] (Ex. 37).
510(k) Disclosure K961421, Jun. 26, 1996 (Synthes) ("K961421") [SNI-0258396] (Ex. 36).
510(k) Disclosure K961413, Aug. 7, 1996 (Synthes) ("K961413") [SNI-0259751] (Ex. 35).
4.5 mm Cannulated Screw Technique Guide, published 1995 (Synthes) [SNI-0259703-714] (Ex. 21).
35 U.S.C. . sctn.282 Notice in the Pennsylvania Action, dated Oct. 10, 2008.
"VariAx TM Distal Radius Locking Plate System", Stryker R, Copyright 2009,12 pages.
"The New Comprehensive Stryker R VariAx TM Distal Radius Locking Plate System", Copyright 2009,20 pages.
"Multiple Offerings of Plates, Screws and Pegs", Small Bone Innovations, Inc., Dec. 2009, 2 pages.
"Less Invasive Stabilization System (LISS) Technique Guide," Synthes (USA) Copyright 2000 (attached as Exhibit K to Amended Answer).
"Cone Drive History and Double Enveloping Technology", http://conedrive.com/history/html., accessed Apr. 20, 2006, 9 pages.
Schuhli Technique Guide 1998, (Synthes) ("Schuhli Guide").
Schmoker, The Locking Reconstruction Plate 2.4-3.2, originally published in Swiss Dent 17,1996.
Schandelmaier, et al., Distal Femur Fractures and Liss Stabilization, Injury, Int. J. Care Injured, vol. 32, Suppl. 3, 55-63, 2001.
Ring, D., et al. "Prospective Multicenter Trial of a Plate for Distal Fixation of Distal Radius Fractures," J. of Hand Surgery, vol. 22a(5), pp. 777-784, Sep. 1997.
Ring, D., et al,"A New Plate for Internal Fixation of the Distal Radius," AO.ASIF Dialogue, vol. IX, issue I, Jun. 1996 [SNI-0254971-973] (Ex. 53).
Reply to Counterclaims, Civil Action No. 03-0084 (E.D. Pa.), filed Jan. 2, 2007.
Rebuttal Expert Report of Russell Parsons, Ph.D., (with Exhibit 1), dated Jul. 15, 2008.
Rebuttal Expert Report of Mari Truman, P.E., (with Exhibit 2), dated May 14, 2008 (Ex. 79).
Rebuttal Expert Report of Eric R. Gozna, M.D., P.ENG., (with Exhibit 1), dated May 13, 2008 (Ex. 56).
Rebuttal Expert Report of Clifford H. Turen, M.D., (with Exhibit 1), dated May 14, 2008.
Rebuttal Expert Report of Charles E. Van Horn (without Exhibits), dated May 12, 2008 (Ex. 77).
Pure Titanium Implants Catalog, published Dec. 1993 (Synthes) ("PTI") [SNI0259670-673] (Ex. 23).
Printout of http://www.aofoundation.org web site, dated May 23, 2007 (attached as Exhibit L to Amended Answer).

(56) References Cited

OTHER PUBLICATIONS

Printout from USFDA 510(k) Premarket Notification Database, dated May 23, 2007, listing Synthes Distal Femur Plate (DFP) System, and bearing 510(k) No. K982727 (attached as Exhibit N to Amended Answer.
Printout from USFDA 510(k) Premarket Notification Database, dated May 22, 2007, listing Synthes 2.4 mm Universal Locking Plate System, and bearing 510(k) No. K961421 (attached as Exhibit R to Amended Answer).
Printout from US FDA 510(k) Premarket Notification Database, dated May 22, 2007, listing Synthes Anatomical Locking Plate System, and bearing 510(k) No. K961413 (attached as Exhibit P to Amended Answer).
Photographs of the Pi plate marked as Little Deposition Exhibit 84.
Photographs of the Bolhofner Distal Femur Plating System (Bolhofner DFPS), Apr. 14, 2008.
Photographs of Synthes Titanium Distal Femur LISS Plate, 9 holes/236 mm—Right, 42.344 (the sample LISS)(SYN-PHY-0000002).
Photographs of Synthes Less Invasive Stabilization System (LISS), screw; (SYN-PHY0000004).
Photographs of Sample Synthes LC-DCP Tibia Plate produced as SYN-PHY-0000014.
Photographs of Sample Synthes LC-DCP CBP produced as SYN-PHY-0000011.
Photographs of sample LC-DCP Condylar Buttress Plate ("CBP") [SYN-PHY-0000001] (Ex. 42).
Perren, S., et al., "Early Temporary Porosis of Bone Induced by Internal Fixation Implants," Clinical Orthopaedics and Related Research, No. 232, Jul. 1988, 139-151.
Perren, et al., "The Limited Contact Dynamic Compression Plate (LC-DCP)," Arch. Orthopaedic & Trauma Surg., 1990, vol. 109, 304-310.
Ms. Truman's Jul. 24, 2008 deposition transcript in the Pennsylvania Action (Ex. 81).
Mr. Van Horn's Jul. 15, 2008 deposition transcript in the Pennsylvania Action (Ex. 78).
Marsh Exhibit C, Declaration of J. Lawrence Marsh, MD., in support of Smith & Nephew's, Inc's Motion for Partial Summary Judgement of Invalidity of Claims 10-12 of U.S. Pat. No. 6,623,486, dated Sep. 9, 2008, pp. 1-20.
Marsh Exhibit B, Supplement to Apr. 9, 2008 Expert Report of J. Lawrence Marsh, MD, Civil Action No. 03-0084, dated May 14, 2008 , pp. 1-19.
Marsh Exhibit A, Releasable 510(k) Search, Aug. 7, 2000, http://web.archive.org/web/19970615015534/www.fda.gov/egibin/htmlscript? 510k.hts+showcat-OR.
Marsh Exhibit A, Initial Expert Report of J. Lawrence Marsh, MD, Civil Action No. 03-0084, dated Apr. 9, 2008 , pp. 1-181.
Marsh Exhibit 1, Curriculum Vitae, Dec. 2006, pp. 1-34.
Marsh Exhibit 1, Affidavit of Christopher Butler dated Aug. 24, 2010.
Manual of Internal Fixation, Techniques Recommended by the AO-ASIG Group, Springer-Verlag, 1991,200-251.
Luthi, U., etal., "Kontackflache zwischen Osteosyntheseplatte und Knochen," Aktuel. Traumatol. 10:131-136,1980 ("Luthi") [SNI-0258572-577] (Ex. 31).
Less Invasive Stabilization System Liss Surgical Technique Proximal Tibia, (Draft), 2000,11 pgs.
Krettek et al.; "Distale Femurfrakturen"; Swiss Surg.; 1998; 4; p. 263-278 with English abstract.
Krettek et al, "LISS less Invasive Stabilization System," AO International Dialogue, vol. 12, Issue I, Jun. 1999.
Koval, k., et al., "Distal Femoral Fixation: A Biomechanical Comparison of the Standard Condylar Buttress Plate, a Locked Buttress Plate, and the 95-Degree Blade Plate," J. of Orthopaedic Trauma, val. 11(7), pp. 521-524, Lippencott-Raven Publishers, Oct. 1997.
Kolodziej, P., et al. "Biomechanical Evaluation of the Schuhli Nut," Clinical Orthopaedics and Related Research, No. 34 7, pp. 79-85, Lippencott-Raven Publishers, Feb. 1988 ("Kolodziej") [SNI-0256042-048] (Ex. 28).
Kassab, et al., "Patients Treated for Nonunions with Plate and Screw Fixation and Adjunctive Locking Nuts," Clinical Orthopaedics and Related Research, 1998, 347, 86-92.
Joint submission setting forth agreed claim construction in the Pennsylvania Action, dated Jul. 31, 2007.
International Patent Application No. PCT/US2008/072894; International Search Report dated Mar. 19, 2009, 18 pages.
Initial Expert Report of J. Lawrence Marsh, M.D., Apr. 9, 2008 (with Exhibits 1-2 and Appendices A-L), dated Apr. 9, 2008 (Ex. 41).
Initial Disclosures of Defendant, Civil Action No. 03-0084 (E.D. Pa), dated Jan. 12, 2007.
Information Disclosure Statement in U.S. Appl. No. 09/660,287, dated Nov. 13, 2000 (attached as Exhibit G to Amended Answer).
Information Disclosure Statement bearing, dated May 4, 2001 (attached as Exhibit F to Amended Answer).
Haas, N.P., et al., "LISS-Less Invasive Stabilization System—A New Internal Fixator for Distal Femur Fractures," OP J., vol. 13(3), pp. 340-344, Georg Thieme Verlag, Dec. 1997 (in English).
Gautier, E., et al., "Porosity and Remodelling of Plated Bone After Internal Fixation: Result of Stress Shielding of Vascular Damage?", Biomaterials and Biomechanics 1983, Elsevier Science Publishers B.V. 1984 ("Gautier").
Expert Report of John F. Witherspoon (w/o Exhibits A-C) in the Pennsylvania Action, dated Apr. 9, 2008; 36 pages.

* cited by examiner

THREADED LOCKING STRUCTURES FOR AFFIXING BONE ANCHORS TO A BONE PLATE, AND RELATED SYSTEMS AND METHODS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application *is a reissue application of U.S. Pat. No. 11,013,541, issued May 25, 2021, which* is related to U.S. patent application Ser. No. 15/926,390,filed on Mar. 20, 2018, in the name of Bosshard, et al.; and Ser. No. 15/940,761, filed Mar. 29, 2018,in the name of Bosshard, et al., the disclosures of each of which are hereby incorporated by reference as if set forth in their entireties herein.

TECHNICAL FIELD

The present invention relates to bone plates and bone anchors for coupling to the bone plates, and particularly relates to threaded locking structures defined within a fixation hole of a bone plate for locking with a head of a bone anchor.

BACKGROUND

Bone plate systems for the internal fixation of bone fractures are well known. Conventional bone plate systems are particularly well-suited to promote the healing of a fracture. A bone anchor, such as a bone screw, is inserted through a fixation aperture or hole in a bone plate and is threaded into bone to compress, neutralize, buttress, tension bend, and/or bridge the fracture ends together. Bone screws that are capable of locking with the bone plate can be employed to transfer loads from one fractured bone part, over a plate, and onto another fractured bone part without drawing the bone against the plate, and to avoid loosening or backing out the bone screws with respect to the plate (which can lead to poor alignment and poor clinical results). One known embodiment of such a screw employs a screw head with external threads for engaging with a corresponding thread on the inner surface of a fixation hole to lock the screw to the plate. These screws, which are hereinafter referred to as "locking screws" or "locking compression screws", and which can include standard-type locking screws that are configured to lock within fixation hole substantially only at a "nominal" orientation whereby the central screw axis is substantially aligned with the central hole axis, as well as "variable-angle" (VA) locking screws that are configured to lock within a fixation hole at either a nominal orientation or an "angulated" orientation whereby the central screw axis is oriented at an acute angle with respect to the respective central hole axis.

SUMMARY

According to an embodiment of the present disclosure, a bone plate includes at least one hole extending through the bone plate from an upper plate surface to a lower plate surface along a central hole axis that is oriented along an axial direction. The at least one hole defined by an interior surface of the bone plate. The interior surface further defining a plurality of columns sequentially located about a circumference of the interior surface and a plurality of recesses located circumferentially between the columns. Each of the columns defines a plurality of thread segments each defining a root, a first thread surface extending from the root to a first crest, and a second thread surface extending from the root to a second crest. At least a portion of the first and second thread surfaces are offset from one another at a thread angle. The thread angle of at least one of the thread segments is in a range of about 5 degrees to about 59 degrees.

BRIEF DESCRIPTION OF THE DRAWINGS

The foregoing summary, as well as the following detailed description of illustrative embodiments of the present application, will be better understood when read in conjunction with the appended drawings. For the purposes of illustrating the locking structures of the present application, there is shown in the drawings illustrative embodiments. It should be understood, however, that the application is not limited to the precise arrangements and instrumentalities shown. In the drawings.

DETAILED DESCRIPTION OF ILLUSTRATIVE EMBODIMENTS

Figure 1:
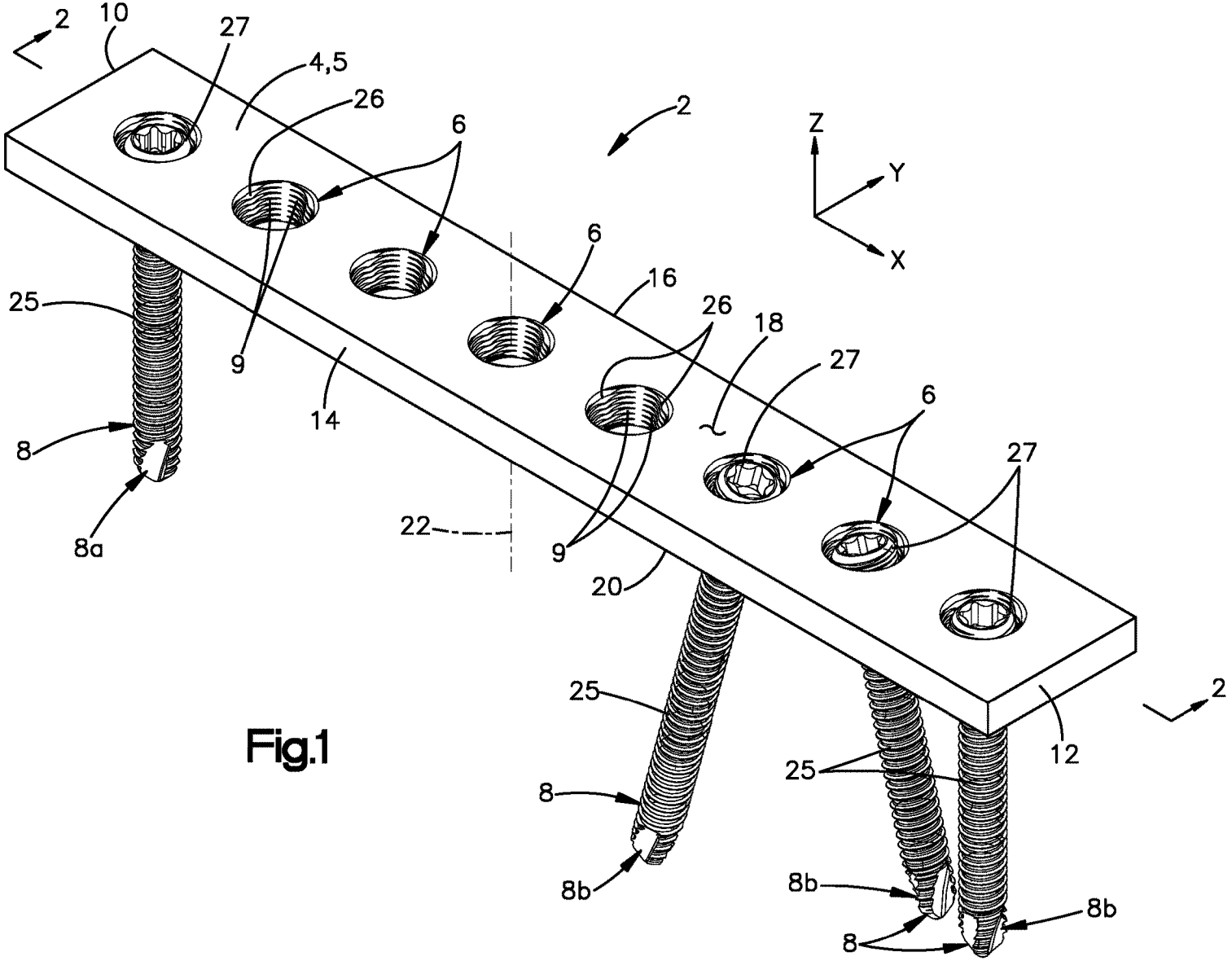
FIG. 1 is a perspective view of a bone fixation system that includes a bone plate and a plurality of locking screws disposed within locking holes of the bone plate, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately" and "substantially", as used herein with respect to dimensions, angles, and other geometries, takes into account manufacturing tolerances. Further, the terms "approximately" and "substantially" can include 10% greater than or less than the stated dimension or angle. Further, the terms "approximately" and "substantially" can equally apply to the specific value stated.

Standard-type locking screws and VA locking screws can both be susceptible to a phenomenon referred to herein as "timing error," whereby factors relating to a bone plating procedure can cause an axial misalignment between external threads on the head of the bone screw relative to corresponding internal threads of a locking hole extending through the bone plate. Moreover, VA locking screws have a tendency to cause cross-threading within a locking hole in which they are inserted, particularly when the VA locking screw is inserted in the locking hole at an angulated orientation. Cross-threading can be caused by the external threads on the screw head not fitting within and thus cross-threading the internal threads of the locking hole. Regions of contact between the crests of the screw head threads and portions of the internal threads, particularly at or near the crests of the internal threads, can be particularly susceptible to cross-threading. Timing error and cross-threading are problematic because they reduce the interference fit (also referred to as the "form-fit") between the internal threads of the aperture and the screw head threads, which can reduce stability between the screw head and the locking hole. The embodiments disclosed herein pertain to locking structures employed within a locking hole, which locking structures define internal threads having geometries that can avoid or at least reduce contact with the screw head crests. The internal threads can also deform in a direction along a central axis of the hole responsive to timing error. In this manner, the threaded locking structures described herein can lock with the heads of both standard-type and VA locking screws in a manner inhibiting or at least reducing cross-threading.

Referring to FIG. 1, a bone fixation system 2 includes a bone plate 4 having a plate body 5 that defines therein one or more fixation holes, such as variable-angle (VA) locking holes 6. The VA locking holes 6 are configured to receive anchor members, such as locking screws 8, for example, that are configured to affix the bone plate 4 to one or more portions of bone. The plate body 5 defines internal threads 9 within the VA locking holes 6. Accordingly, the internal threads 9 can also be referred to as "plate hole threads" or simply "plate threads" or "hole threads." The hole threads 9 traverse locking structures, such as columns 26, defined within the VA locking holes 6. Thus the locking structures and columns 26 can be referred to as "threaded locking structures" and "threaded columns", respectively. The threaded columns 26 are configured such that, during insertion of a locking screw 8 within the VA locking hole 6, a screw shaft 25 of the locking screw 8 bypasses the columns 26, which in turn engage external threads 29 on the screw head 27 of the locking screw 8 in a manner providing enhanced locking engagement between the locking screw 8 and the bone plate 4, as set forth in more detail below.

The bone plate 4 can be a bridge plate, as shown, although other bone plate types and configurations are within the scope of the present disclosure. The plate body 5 can define a first end 10 and a second end 12 spaced from each other along a longitudinal direction X and a first lateral side 14 and a second lateral side 16 spaced from each other along a lateral direction Y that is substantially perpendicular to the longitudinal direction X. The bone plate 4 can also define an upper plate surface 18 configured to face away from the bone and an opposed lower plate surface 20 configured to face the bone. The upper and lower plate surfaces 18, 20 are spaced from each other along a vertical direction Z substantially perpendicular to each of the longitudinal direction X and the lateral direction Y.

It is to be appreciated that, as used herein, the terms "longitudinal", "longitudinally", and derivatives thereof refer to the longitudinal direction X; the terms "lateral", "laterally", and derivatives thereof refer to the lateral direction Y; and the terms "vertical", "vertically", and derivatives thereof refer to the vertical direction Z.

The VA locking holes 6 extend axially from the upper plate surface 18 to the lower plate surface 20 along a central hole axis 22. In the depicted embodiment, the central hole axis 22 is oriented along the vertical direction Z, although in other embodiments the central hole axis 22 of one or more of the VA locking holes 6 can be oriented at an oblique angle with respect to the vertical direction Z. As used herein, an "axial direction" is defined as the direction along which the central hole axis 22 extends. Moreover, the directional terms "axial", "axially", and derivatives thereof refer to the axial direction. Thus, as used herein, the directional term "axially upward" and derivatives thereof refers to the axial direction from the lower plate surface 20 toward the upper plate surface 18. Conversely, the term "axially downward" and derivatives thereof refers to the axial direction from the upper plate surface 18 toward the lower plate surface 20. Thus, "axially upward" and "axially downward" are each mono-directional components of the "axial direction", which is bi-directional.

The plate body 5 and the locking screws 8 can each comprise one or more biocompatible materials, such as titanium, titanium alloys (e.g., titanium-aluminum-niobium (TAN) alloys, such as Ti-6Al-7Nb), stainless steel, cobalt base alloys, composite materials, and polymeric materials and/or ceramic materials, by way of non-limiting examples. Preferably, the plate body 5 material is less hard than the locking screw 8 material. This parameter contributes to the locking characteristics described below. In one example embodiment, the plate body 5 primarily or entirely comprises titanium and the locking screws 8 primarily or entirely comprise TAN.

Figure 2:
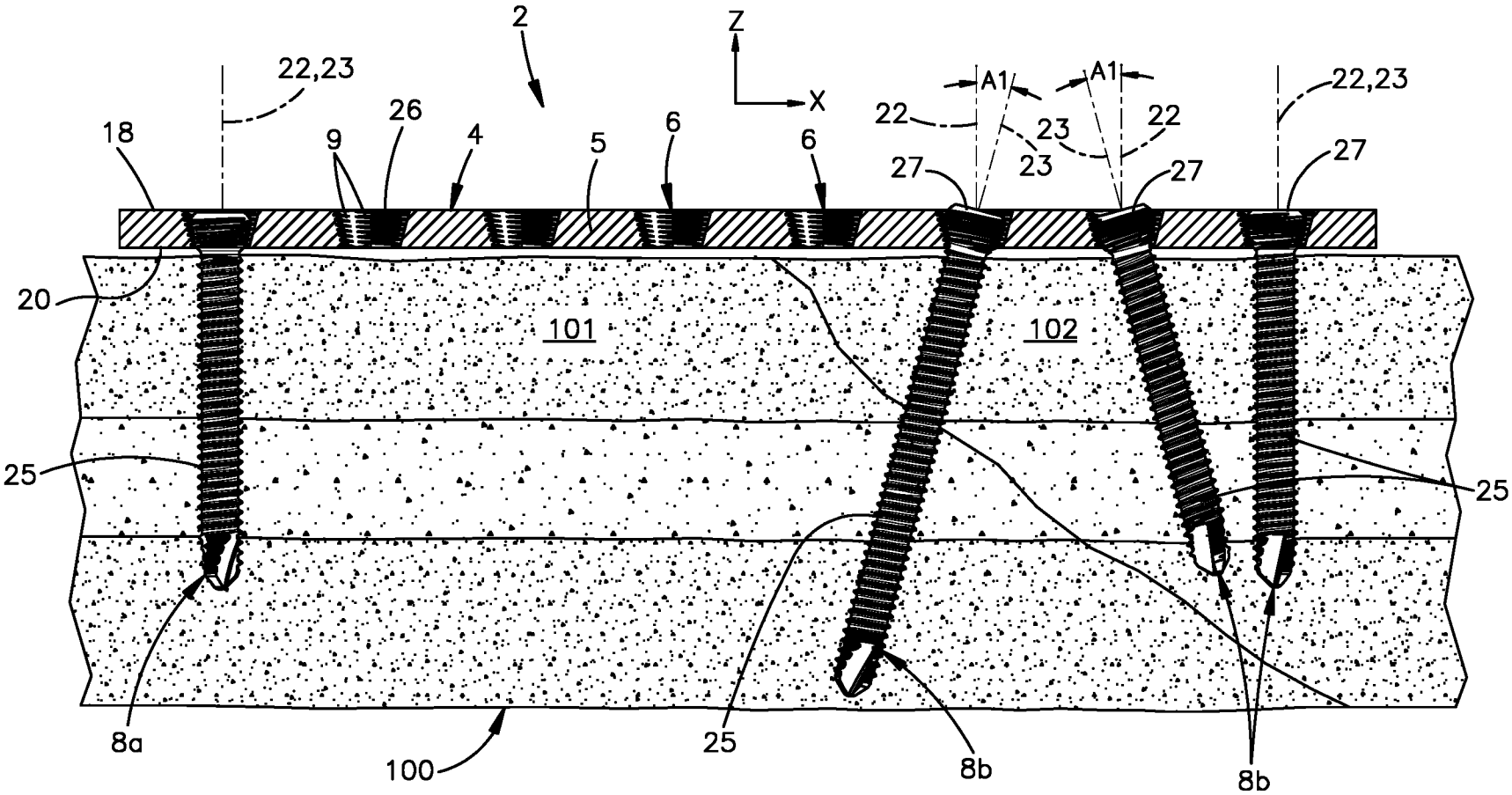
FIG. 2 is a sectional side view of the bone fixation system taken along section line 2-2 in FIG. 1 affixed to a plurality of bone segments.

Referring now to FIG. 2, the VA locking holes 6 can be configured to provide enhanced affixation with multiple types of locking screws 8, including standard-type locking screws 8a and VA locking screws 8b, each optionally having various lengths, so as to allow a physician to implant the bone plate 4 to one or more bones or bone segments as desired. By way of non-limiting example, as shown, the bone plate 4 can be coupled to a long-bone 100 via locking screws 8a, 8b in a manner affixing fractured segments 101, 102 of the bone together. The VA locking holes 6 described herein can lock with standard-type locking screws 8a at a nominal orientation whereby a central screw axis 23 thereof is substantially aligned with the central hole axis 22. The VA locking holes 6 can also lock with VA locking screws 8b at either a nominal orientation or an "angulated" orientation whereby the central screw axis 23 is oriented at an acute angle A1 with respect to the respective central hole axis 22. Acute angle A1 can also be referred to as the "angle of angulation" or simply the "angulation." Both types of locking screws 8a, 8b and their locking functionalities are described more fully in U.S. Pat. No. 9,314,284, issued Apr. 19, 2016, in the name of Chan et al. (the "Chan Reference"), the entire disclosure of which is incorporated by reference herein, as well as U.S. patent application Ser. Nos. 15/926,390 and 15/940,761, referenced above.

During a bone plating operation, the screw shaft 25 of a locking screw 8 can be inserted through one of the VA locking holes 6 and driven into the underlying bone 100. In particular, rotation of the locking screw 8 causes its threaded screw head 27 to threadedly mate with the VA locking hole 6. As a result, the screw head 27 fastens the bone plate 4 to the underlying bone 100 substantially without applying a compressive force onto the bone plate 4 against the underlying bone 100. The bone plate 4 can be spaced from the underlying bone 100 when locked to the threaded screw head 27. Alternatively, the bone plate 4 can abut the underlying bone 100 when locked to the threaded screw head 27.

It is to be appreciated that, during a plating operation, the first locking screw 8 inserted through one of the VA locking holes 6 and into underlying bone 100 has the benefit of being able to generally mate with the hole threads 9 so that crests of the screw head thread 29 advance helically substantially along the troughs of the hole threads 9. However, once the first locking screw 8 is locked to the bone plate 4 thereby fastening the plate 4 to the underlying bone 100, the subsequent locking screws 8 often lack the ability to have their external thread crests advance helically along the hole thread 9 troughs. This results because, once the screw shafts 25 of these subsequent locking screws 8 advance through the VA locking holes 6 and threadedly purchase into the underlying bone 100, the relative axial positions of the screw head threads 29 and the hole threads 9 are substantially a function of the screw's threaded purchase with the underlying bone 100. This axial misalignment of the screw head threads 29 relative to the hole threads 9 is referred to herein as "timing error." As described in more detail below, the threaded columns 26, and thus the hole threads 9, can be configured to deform axially to accommodate the timing error associated with locking screws 8. Such deformation can inhibit or at least reduces cross-threading within the VA locking holes 6.

Figure 3:
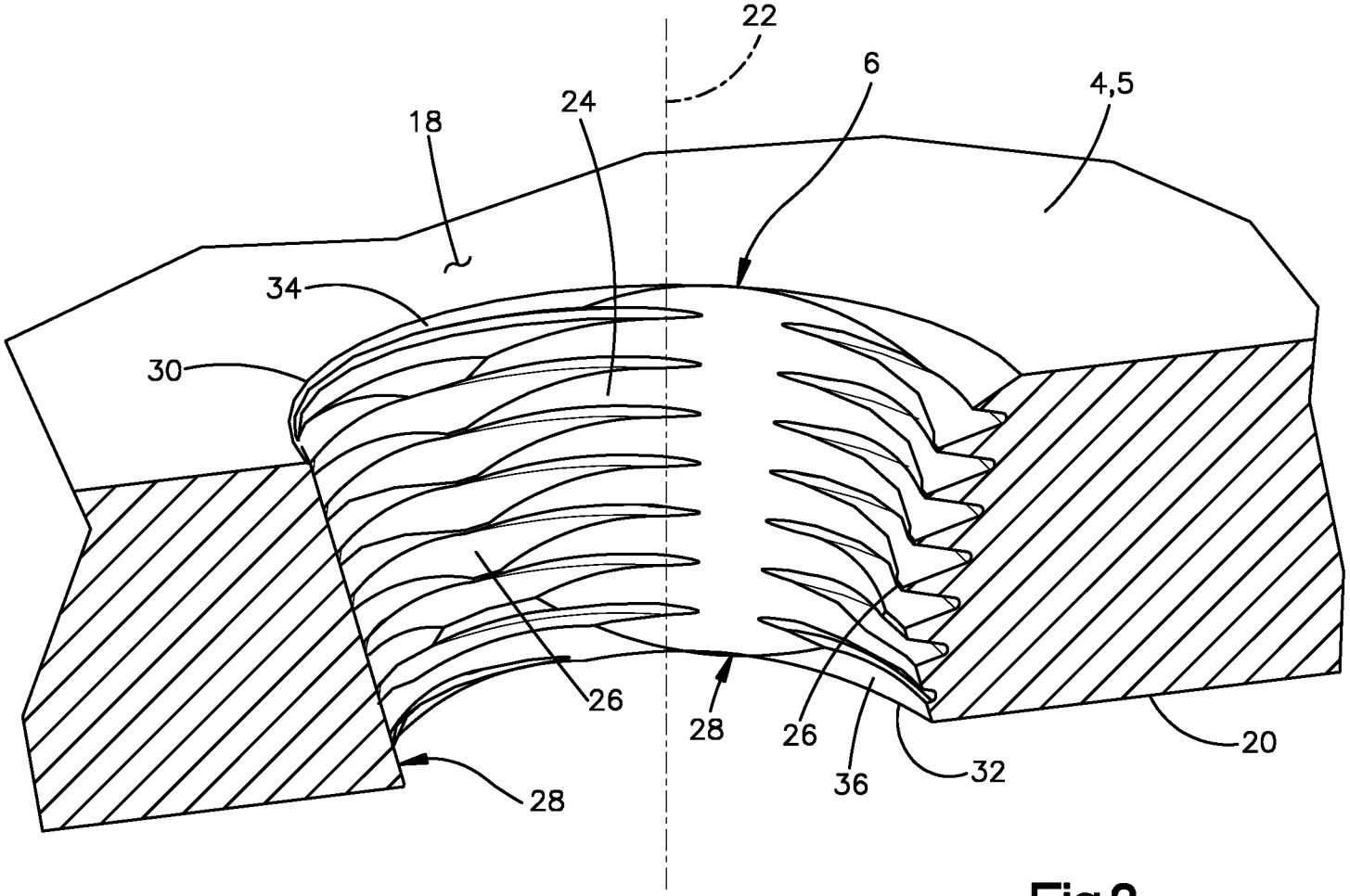
FIG. 3 is a sectional perspective view of a locking hole of the bone plate of FIGS. 1 and 2.
Figure 4:
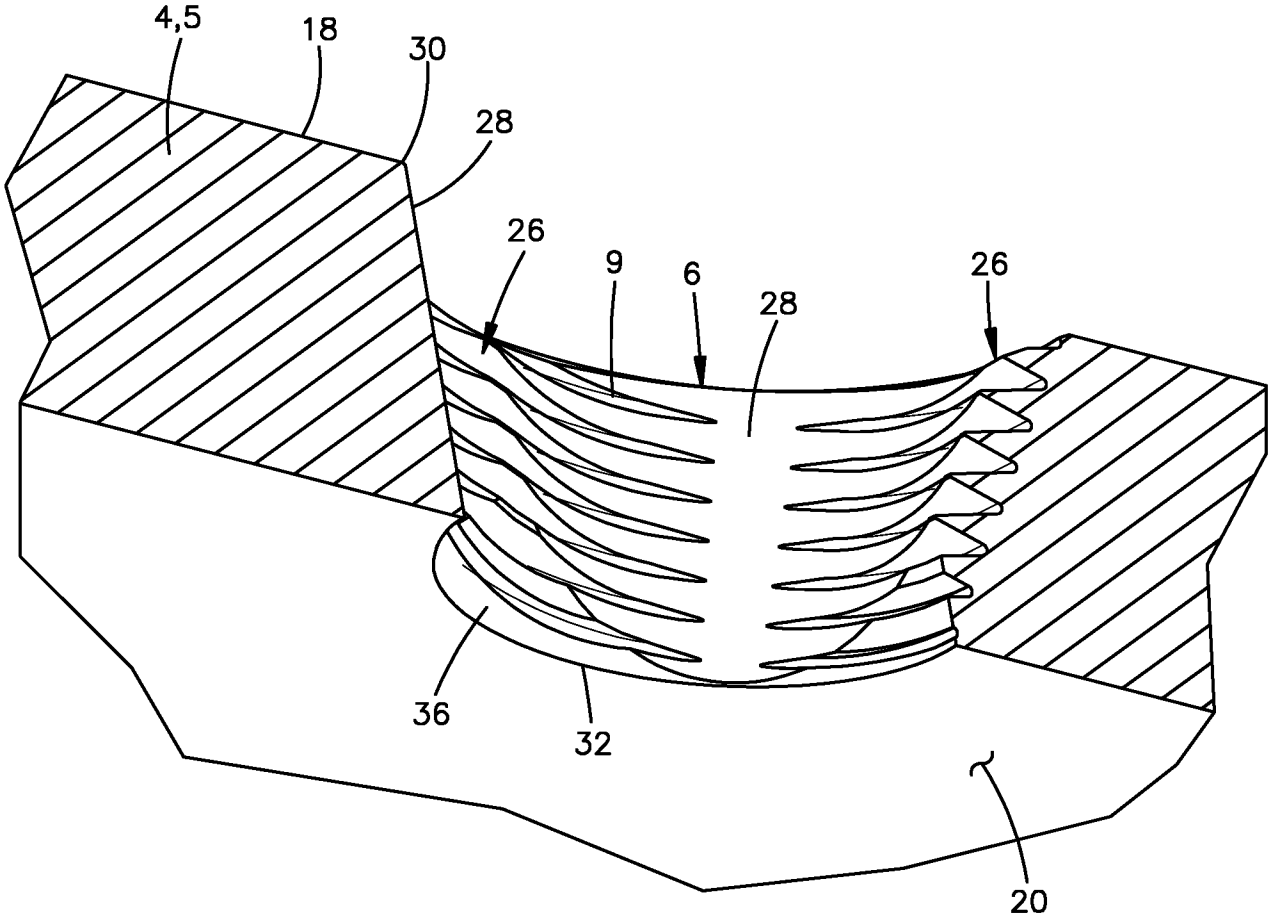
FIG. 4 is another sectional perspective view of the locking hole of FIG. 3.

Referring now to FIGS. 3 and 4, each of the VA locking holes 6 can be defined by an interior surface 24 of the plate body 5. Alternatively, the interior surface 24 can be defined by an insert fitted within an axial aperture of the plate body 5. Typically, at least a portion of the interior surface 24 is tapered as it extends axially downward. Thus, the interior surface 24 is configured to prevent the screw head 27 from passing completely through the VA locking hole 6.

The interior surface 24 can define the columns 26. The columns 26 extend axially between the upper and lower plate surfaces 18, 20. Within each (or at least some of) the VA locking holes 6, the columns 26 are sequentially located about a circumference of the interior surface 24. The interior surface 24 also defines a plurality of recesses 28 sequentially located circumferentially between the columns 26. The recesses 28 extend axially between the upper and lower plate surfaces 18, 20. The columns 26 and recesses 28 can be evenly spaced about the circumference of the interior surface 24 within the VA locking hole 6. However, in other embodiments, the columns 26 and/or recesses 28 can be un-evenly spaced about the circumference of the VA locking hole 6.

The interior surface 24 can define an upper perimeter 30 of the VA locking hole 6 at an interface with the upper plate surface 18 and a lower perimeter 32 of the VA locking hole 6 at an interface with the lower plate surface 20. The upper and lower perimeters 30, 32 can each be circular in shape, although other shapes are within the scope of the present disclosure. The interior surface 24 can also define a lead-in surface 34 that tapers axially downward from the upper perimeter 30 to one or more of the columns 26. As shown, the lead-in surface 34 can be circumferentially interrupted by one or more of the recesses 28. Alternatively, the lead-in surface 34 can extend circumferentially continuously and uninterrupted along a full revolution about the central hole axis 22. The interior surface 24 can also define an undercut surface 36 that tapers axially upward from the lower perimeter 32. The undercut surface 36 can extend circumferentially continuously and uninterrupted along a full revolution about the central hole axis 22. Alternatively, the undercut surface 36 can be circumferentially interrupted by one or more of the recesses 28.

Figure 5:
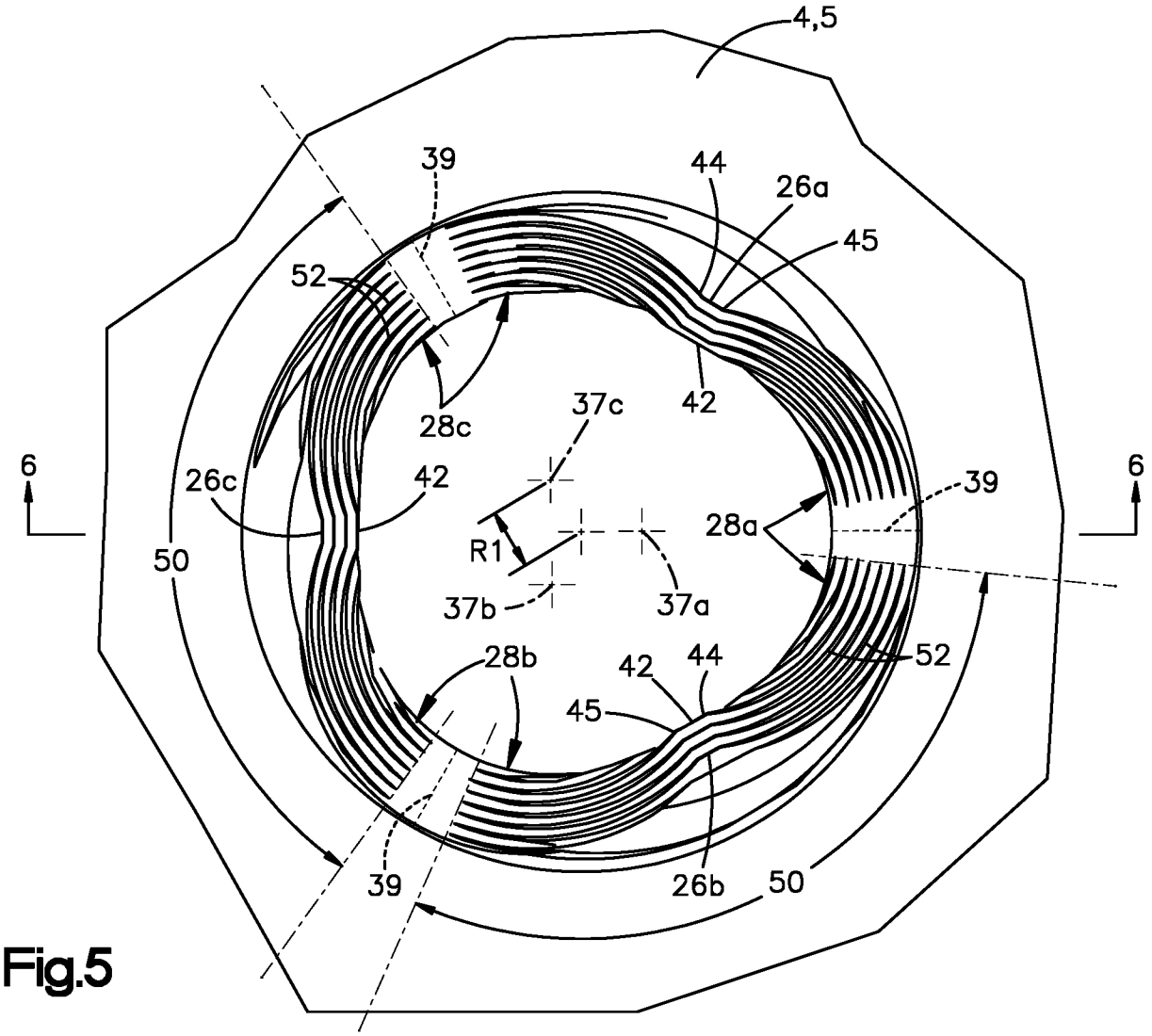
FIG. 5 is a top view of the locking hole of FIG. 3.
Figure 6:
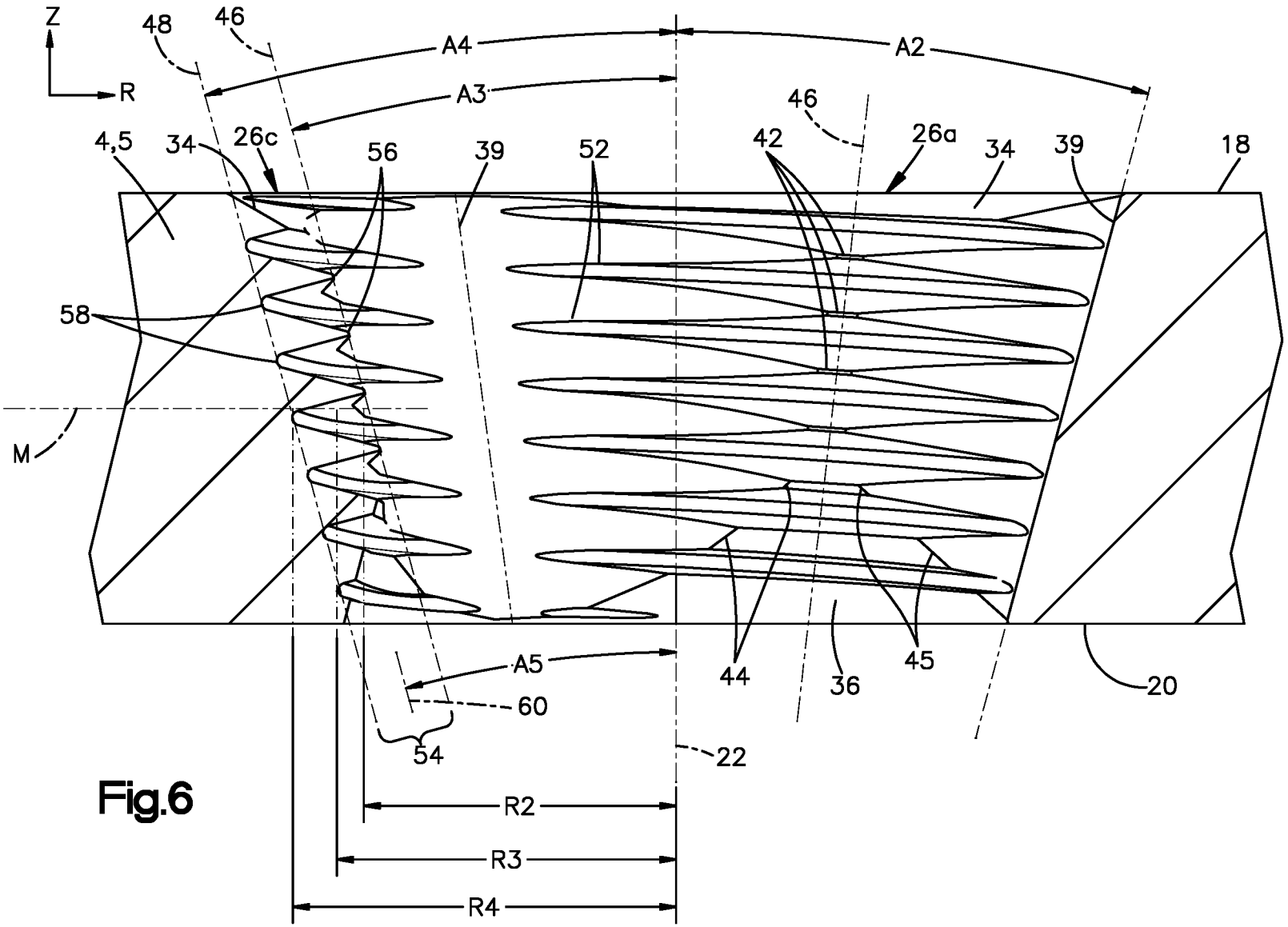
FIG. 6 is a side sectional view of the locking hole taken along section line 6-6 in FIG. 5, showing a threaded locking structure defined by an interior surface of the locking hole, wherein the threaded locking structure is configured to lock with a locking bone screw.

Referring now to FIGS. 5 and 6, in an example embodiment, the VA locking hole 6 can include three (3) columns 26 and three (3) recesses 28 evenly spaced about the central hole axis 22. The columns 26 can include a first column 26a, a second column 26b, and a third column 26c evenly spaced about the central hole axis 22. The recesses 28 can include: a first recess 28a located circumferentially between the first and second columns 26a, 26b; a second recess 28b located circumferentially between the second and third columns 26b, 26c; and a third recess 28c located circumferentially between the third and first columns 26c, 26a. It is to be appreciated that in other embodiments there can be fewer than three (3) or more than three (3) columns 26 and recesses 28, respectively.

As shown in FIG. 5, the first recess 28a can define a first recess axis 37a, the second recess 28b can define a second recess axis 37b, and the third recess 28c can define a third recess axis 37c. Each recess axis 37a-37c can be parallel with the central hole axis 22, although other recess axis 37a-37c orientations are possible. Each recess axis 37a-37c can also be radially spaced from the central hole axis 22 by radial distance R1. Each of the recesses 28a-28c can define a portion of a downward-tapering frusto-conical shape that defines a central cone axis coincident with the respective recess axis 37a-37c. The frusto-conical shapes of the recesses 28a-28c can be substantially identical. In the illustrated embodiment, the frusto-conical shapes are each a frustum of a right circular cone; however other recess geometries can be employed. Each recess 28 defines a radially-outermost region or trough 39. Each trough 39 can lie in a plane that also includes the central hole axis 22. As shown in one such plane in FIG. 6, the troughs 39 can be oriented at an acute angle A2 in a range of about 5 degrees to about 30 degrees relative to the central aperture axis 22. The recesses 28 can be configured such that the troughs 39 define the radially outermost locations of the VA locking hole 6, as measured in any reference plane that extends through the VA locking hole 6 and is orthogonal to the central hole axis 22.

Each column 26 can define a first surface 42 substantially facing the central hole axis 22. The first surface 42 can also be referred to as an "innermost surface" of the column 26. The first surfaces 42 of the columns 26 can extend generally axially between the upper and lower plate surfaces 18, 20. The first surface 42 of each column 26 can also extend between a first side 44 and a circumferentially opposed second side 45 of the column 26. The first and second sides 44, 45 of each column 26 can define interfaces between the column 26 and the circumferentially adjacent recesses 28. For example, the first side 44 of the first column 26a can define an interface between the first column 26a and the third recess 28c; the second side 45 of the first column 26a can define an interface between the first column 26a and the first recess 28a; the first side 44 of the second column 26b can define an interface between the second column 26b and the first recess 28a; and so forth along the circumference of the interior surface 24. The first surfaces 42 of the columns 26 can collectively define segments of another downward-tapering frusto-conical shape that defines a central cone axis coincident with the central hole axis 22.

The hole threads 9 extend through the columns 26 and at least portions of the recesses 28 along one or more thread paths between the upper and lower plate surfaces 18, 20. The one or more thread paths can be a single thread path (i.e., single-lead), a pair of non-intersecting thread paths (i.e., double-lead), or three or more thread paths (e.g., triple-lead, etc.). The thread paths can be helical. Portions of the recesses 28 can optionally circumferentially interrupt the hole threads 9 so as to define a plurality of threaded regions 50 spaced about the circumference of the VA locking hole 6, as shown. Each threaded region 50 carries one or more thread segments 52 extending along the thread path(s). Axially aligned ones of the thread segments 52 can traverse a respective one of the columns 26 so as to define column threads 54.

With reference to FIG. 6, the first surface 42 of each column 26 can define a column centerline 46 that is disposed circumferentially equidistantly between the first and second sides 44, 45 of the column 26. The column centerlines 46 of the columns 26 can lie in respective planes that also include the central hole axis 22. In each column, the column centerline 46 can extend along the crests 56 of the column threads 54. Thus, the column centerline 46 can also be referred to as the "crest centerline" of the respective column threads 54. A root centerline 48 can extend along the roots 58 of the column threads 54. In each column 26, the crest centerline 46 and the root centerline 48 can both lie in a single plane that includes the hole axis 22. The crest centerline 46 can be oriented at an acute angle A3 in a range from about 5 degrees to about 30 degrees relative to the central aperture axis 22. The root centerline 48 can also be oriented at an acute angle A4 in a range from about 5 degrees to about 30 degrees relative to the central aperture axis 22. The crest and root centerlines 46, 48 can be parallel, as shown. The column threads 54 can also define a thread midline 60, which can lie in a common plane with the crest and root centerlines 46, 48 and the central hole axis 22. The thread midline 60 can define an acute angle A5 in a range from about 5 degrees to about 30 degrees relative to the central aperture axis 22. In the illustrated embodiment, the thread midline 60 is parallel with, and equidistantly spaced between, the crest centerline 46 and the root centerline 48. It is to be appreciated that, in other embodiments, the crest and root centerlines 46, 48 of a column 26 can be oriented at an oblique angle relative to one another.

The crest centerline 46 can be radially spaced from the central hole axis 22 by a radial distance R2 measured along a reference plane M that is orthogonal to the central hole axis 22 and located at the vertical center of the VA locking hole 6. Thus, the reference plane M can be characterized as the axial "mid-plane" of the VA locking hole 6. The thread midline 60 can be radially spaced from the central hole axis 22 by a distance R3 measured along the hole mid-plane M. The root centerline 48 can be radially spaced from the central hole axis 22 by a distance R4 measured along the hole mid-plane M. Distance R2 can be characterized as the mean crest radius of the column threads 54. Distance R3 can be characterized as the mean radius of the column threads 54. Distance R4 can be characterized as the mean root radius of the column threads 54.

Figure 7:
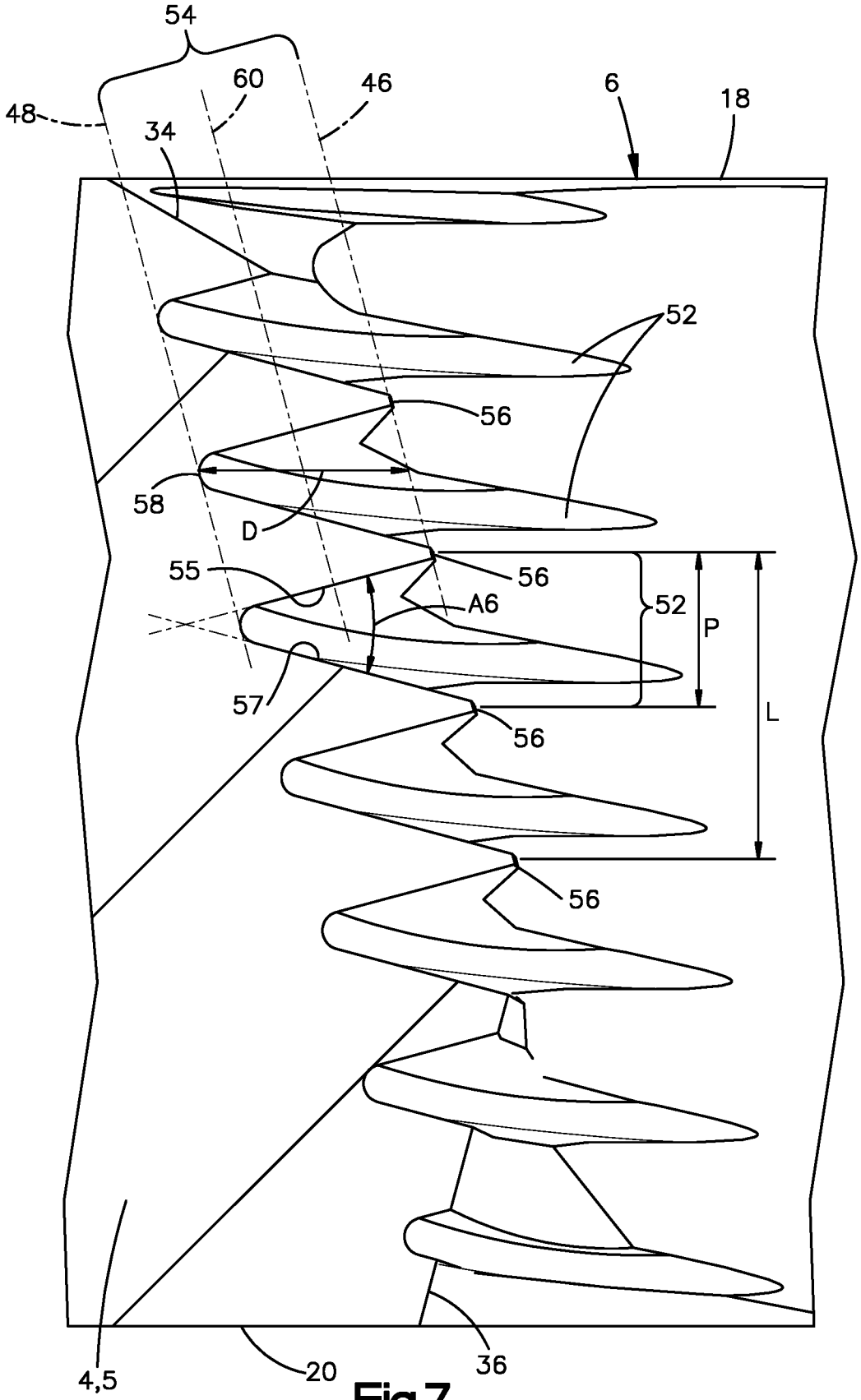
FIG. 7 is an enlarged sectional view of the threaded locking structure shown in FIG. 6.

Referring now to FIG. 7, each of the thread segments 52 can define a root 58, a first thread surface 55 extending from the root 58 to a first, axially upper crest 56. Each thread segment 52 can also define a second thread surface 57 extending from the root 58 to a second, axially lower crest 56. The first and second thread surfaces 55, 57 are offset from one another at an angle A6, which defines the thread angle of the column threads 54. The thread angle A6 can be in a range of about 20 degrees to about 40 degrees, preferably in a range of about 25 degrees to about 35 degrees, and more preferably about 30 degrees.

In embodiments where the hole threads 9 are double-lead threads, the column threads 54 can define a thread pitch P in a range of 0.2 mm to about 0.6 mm and preferably about 0.4 mm and a thread lead L in a range of about 0.4 mm to about 1.2 mm and preferably about 0.8 mm, each measured along the axial direction. The column threads 54 can also define a thread depth D measured from the crest centerline 46 to the root centerline 48 along the radial direction R. The pitch P and lead L of the hole threads 9 are preferably equivalent to the pitch and lead of the screw head threads 29.

Figure 8:
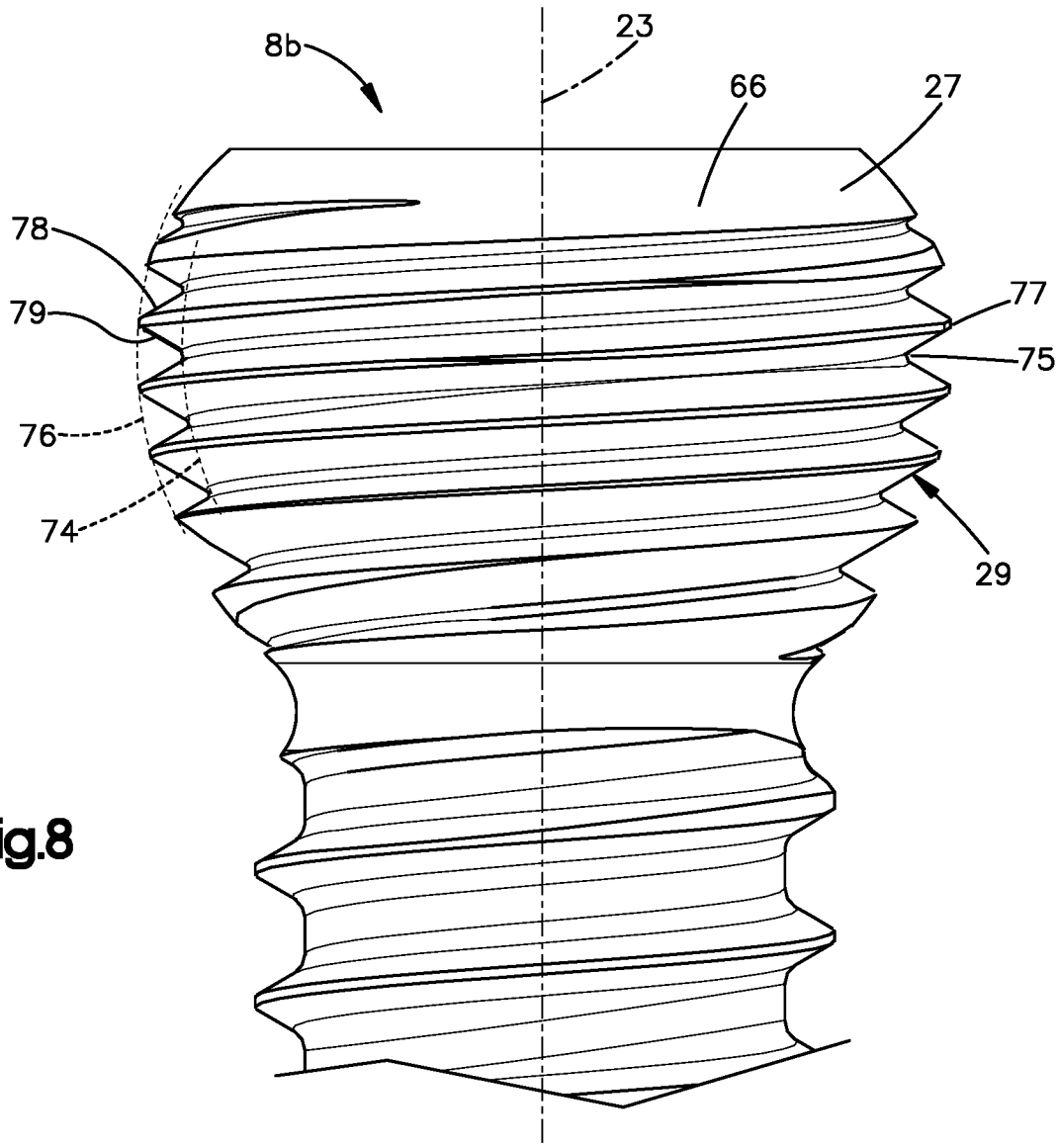
FIG. 8 is a side view of a head of a variable-angle (VA) locking screw configured to be locked to the bone plate of FIG. 1 within one of the locking holes.

Referring now to FIG. 8, the VA locking hole 6 described above can be configured to provide beneficial mating characteristics with the screw head 27 of the standard-type locking screw 8a (FIG. 2) and the VA locking screw 8b. The screw head 27 of the VA locking screw 8b can have a generally spherical outer surface 66 that defines the external screw head threads 29. The external screw head threads 29 of the VA locking screw 8b define a first thread profile 74 measured at the thread roots 75 and a second thread profile 76 measured at the thread crests 77. As depicted, the threads profiles 74, 76 of the VA locking screw 8b are generally spherical, which provides the screw head 27 with a locking functionality as it advances within the VA locking hole 6. The external screw head threads 29 have a thread angle of about 60 degrees.

With reference to FIGS. 9 through 17, threaded engagement between the VA locking holes 6 and the VA locking screw 8b will now be described. Although the following description of threaded engagement between the screw head threads 29 and the hole threads 9 is made in reference to a single threaded column 26, it is to be appreciated that the other columns 26 in the VA locking hole 6 can engage with the screw head threads 29 in a similar, cooperative manner.

Figure 9:
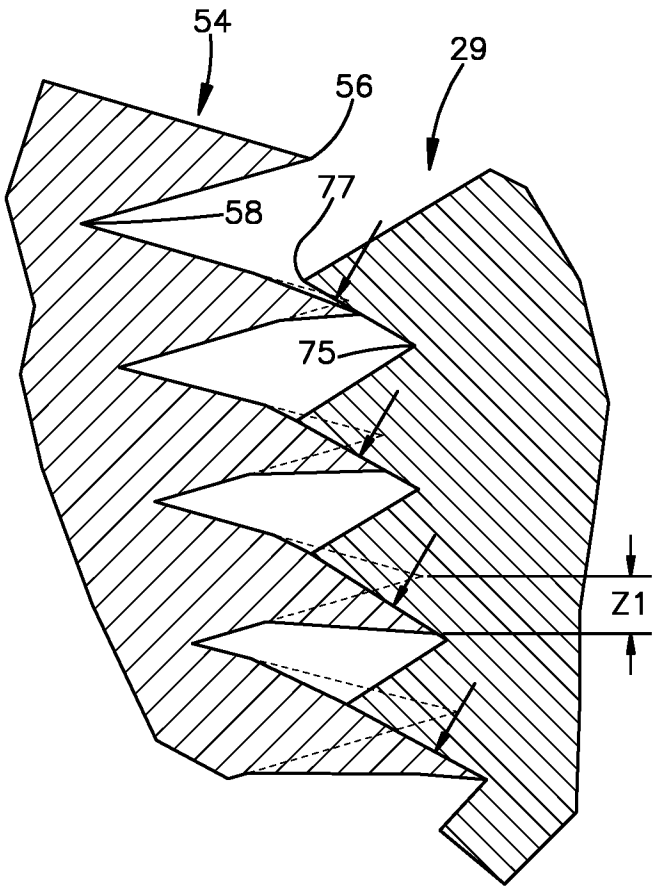
FIG. 9 is a sectional side view showing threaded engagement and "timing-error" compensation between external threads on the head of the VA locking screw shown in FIG. 8 and internal threads of the locking structure shown in FIG. 6 during locking.

Referring now to FIG. 9, axial deformation of the column threads 54 is shown, which can compensate for timing error between the VA locking hole 6 and the VA locking screw 8b. In this example, the timing error causes the screw head threads 29 to transmit axially downward forces to the column threads 54. The column threads 54 disclosed herein are configured to have axial flexibility, particularly at the crests 56 thereof. This allows the column threads 54 to deform axially responsive to the transmitted axially downward forces. One or more of the crests 56 of the column threads 54 can be configured to deform downward or upward, and non-destructively, at a maximum axial deformation distance Z1 that is at least substantially equivalent to one half of the thread pitch P or to one half of the thread lead L divided by the number of leads. Accordingly, the maximum axial deformation distance Z1 can be expressed by the equation: $Z1=0.5(P)=0.5(L)/(N_{Leads})$. According to one example embodiment, the lead L is 0.8 mm, the pitch P is 0.4 mm, the column threads 54 are double-lead (N=2), and the resultant maximum axial deformation Z1 of the thread crest 56 is 0.2 mm. The axial deformability of the column threads 54 can avoid, or at least reduce the timing-error and thus, avoid or at least reduce the occurrence of cross-threading within the VA locking hole 6.

Figure 10:
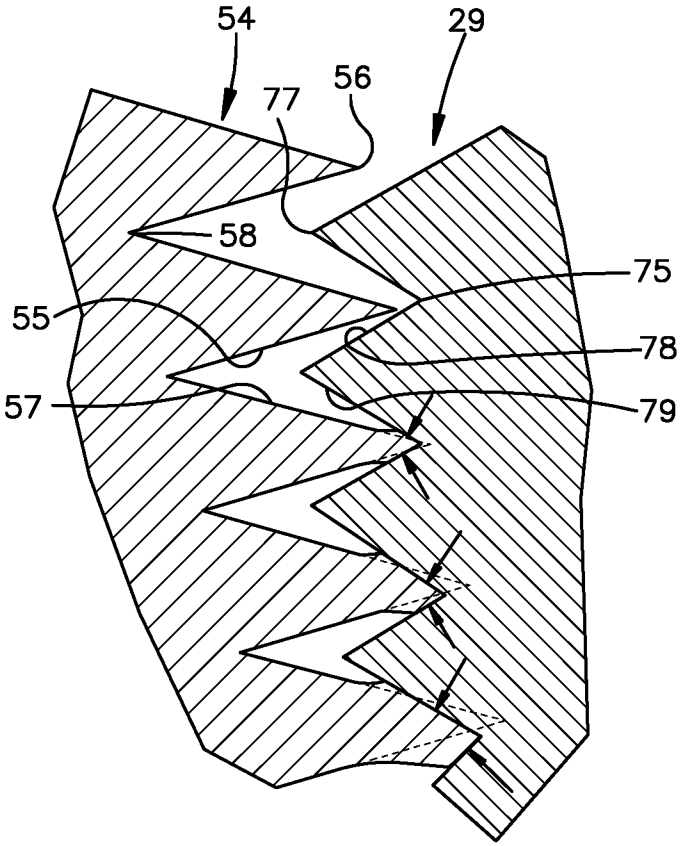
FIG. 10 is a sectional side view showing another threaded engagement and plastic and elastic deformation between the external threads on the head of the VA locking screw and internal threads of the locking structure shown in FIG. 6 after locking.

Referring now to FIG. 10, radially outward deformation of the column threads 54 is shown, such as, for example, to lock to the VA locking screw 8b to the bone plate 4. In this example, timing error is not present. During screw insertion in the VA locking hole 6, the column threads 54 engage the screw head threads 29 in an interconnecting manner so as to substantially achieve a form-fit in the VA locking hole 6. In this form-fit, contact between the hole threads 9 and the screw head threads 29 can occur predominantly via engagement between the crests 56 of one or more of the column threads 54 and the roots 75 of one or more associated screw head threads 29. This type of crest 56-to-root 75 contact is at least partially provided by the shallower thread angle A6 of the column threads 54 relative to the thread angle of the screw head threads 29.

Once form-fit is achieved, further rotational advancement of the VA locking screw 8b with respect to the column threads 54 can commence deforming the one or more column threads 54, preferably at the crests 56. This deformation occurs primarily radially outward, although some measure of axial and/or circumferential deformation can occur, mostly when a timing-error is present. Moreover, the radial deformation can include plastic and elastic deformation, which compresses the one or more column threads 54 in a manner exerting a reactive compressive force against the associated screw head threads 29, primarily at the roots 75 thereof. The plastic and elastic radial deformability of the column threads 54 can also reduce cross-threading within the VA locking hole 6. Additionally, the thread angle A6 and thread depth D can provide clearance for the screw head crests 77 within the column threads 54, which can reduce contact between the column threads 54 and the screw head crests 77, thereby further reducing cross-threading.

Furthermore, as the one or more column threads 54 deforms radially, the total engaged surface area between the column threads 54 (including at the crests 56 and the upper and lower surfaces 55, 57) and the screw head threads 29 (including at the roots 75 and the upper and lower surfaces 78, 79) increases. In this manner, the physical interface between the column threads 54 and the screw head threads 29, and thus between the plate 4 and the VA locking screw 8b, also increases, providing a more stable bone fixation system 2. This principle of deforming the crests 56 of the column threads 54 via engagement with the roots 75 of the screw head threads 29 is achieved, at least in part, by use of a harder locking screw 8 material relative to the hardness of the plate body 5 material as mentioned above.

With reference to FIG. 11 through 16, engagement between the VA locking hole 6 and VA locking screws 8b at various angulations will now be described.

Figure 11:
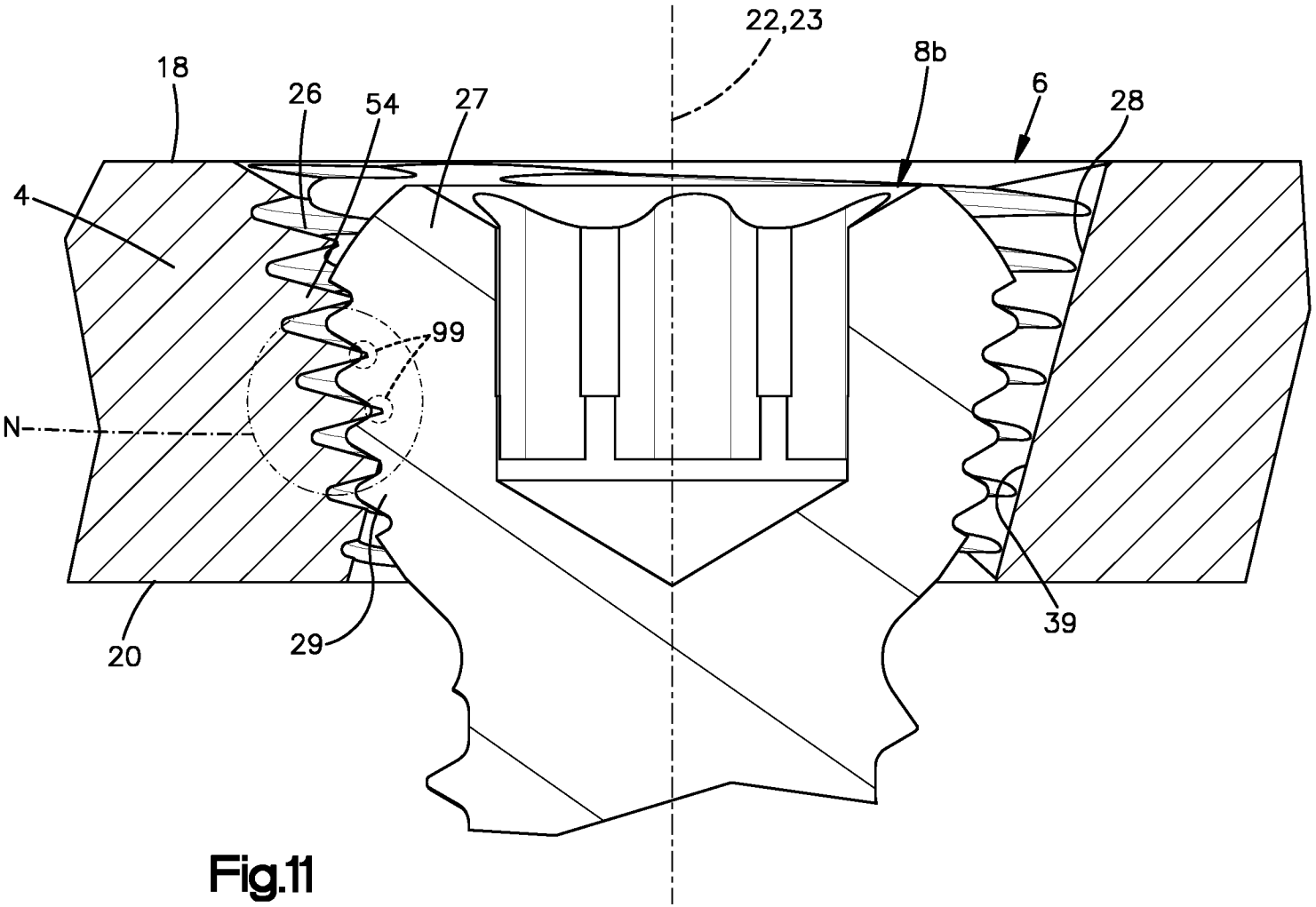
FIG. 11 is a sectional side view of the head of the VA locking screw of FIG. 8 during locking at a nominal orientation within the locking hole shown in FIG. 6.
Figure 12:
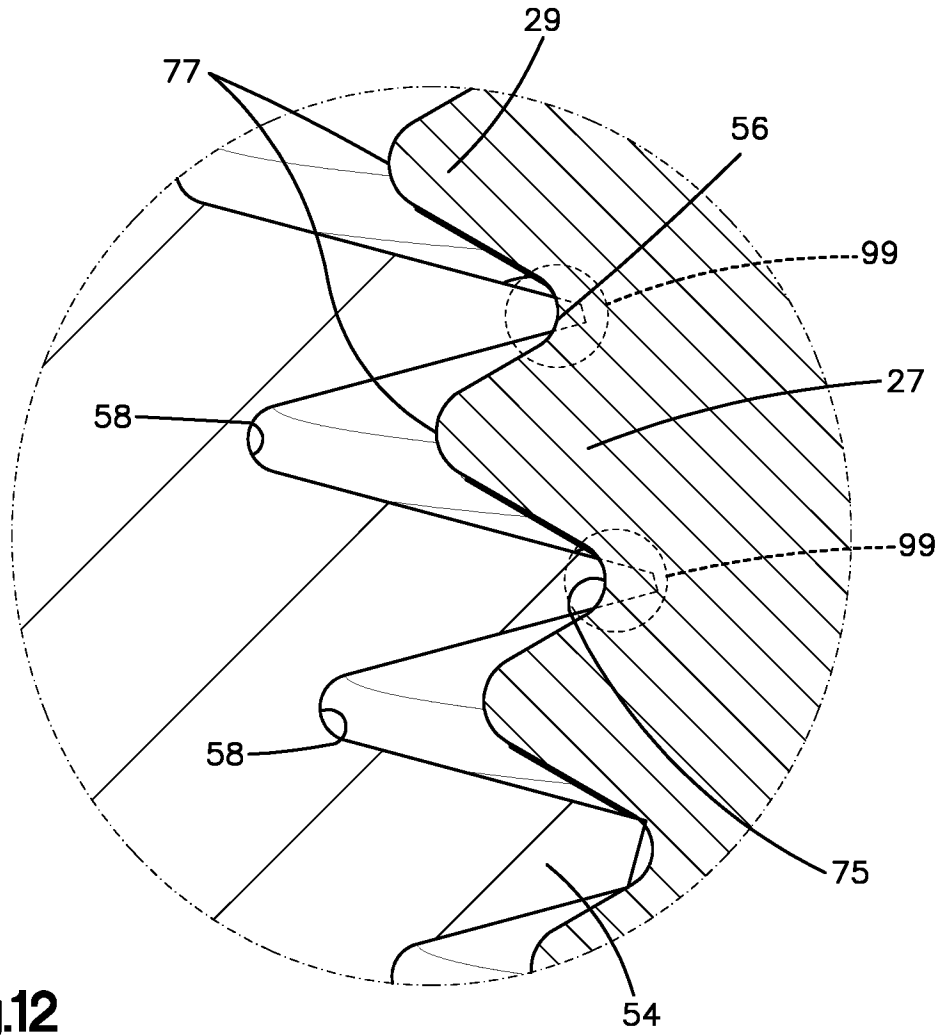
FIG. 12 is an enlarged view of region N in FIG. 11, showing deformation of the internal threads of the locking structure against the external threads on the head of the VA locking screw during locking at a nominal orientation.

Referring now to FIG. 11, the VA locking screw 8b can be locked within the VA locking hole 6 of the present embodiment at a nominal orientation and such that the thread crests 56 of the plate hole threads 9 undergo an elastic and plastic deformation, dependent on the applied locking torque. As shown in FIG. 11, the applied locking torque is still small and the deformation of the thread crests 56 just started. With a further advancement of the screw 8b along its central screw axis 23, the locking torque and the deformation of the thread crests 56 will increase further. Furthermore, as shown more clearly in the magnified view of FIG. 12, such locking can start at one and continue to two of the thread segments 52 of a column 26 in contact with the screw head threads 29 at the crest centerline 46, as shown at interference regions 99. This beneficial locking mechanism is provided by at least in part by the plastic and elastic radial deformation of the column thread(s) 54 responsive to contact with the screw head threads 29. It is to be appreciated that the VA locking hole 6 can engage the head 27 of a standard-type locking screw 8a inserted at a nominal orientation in a generally similar manner.

Figure 13:
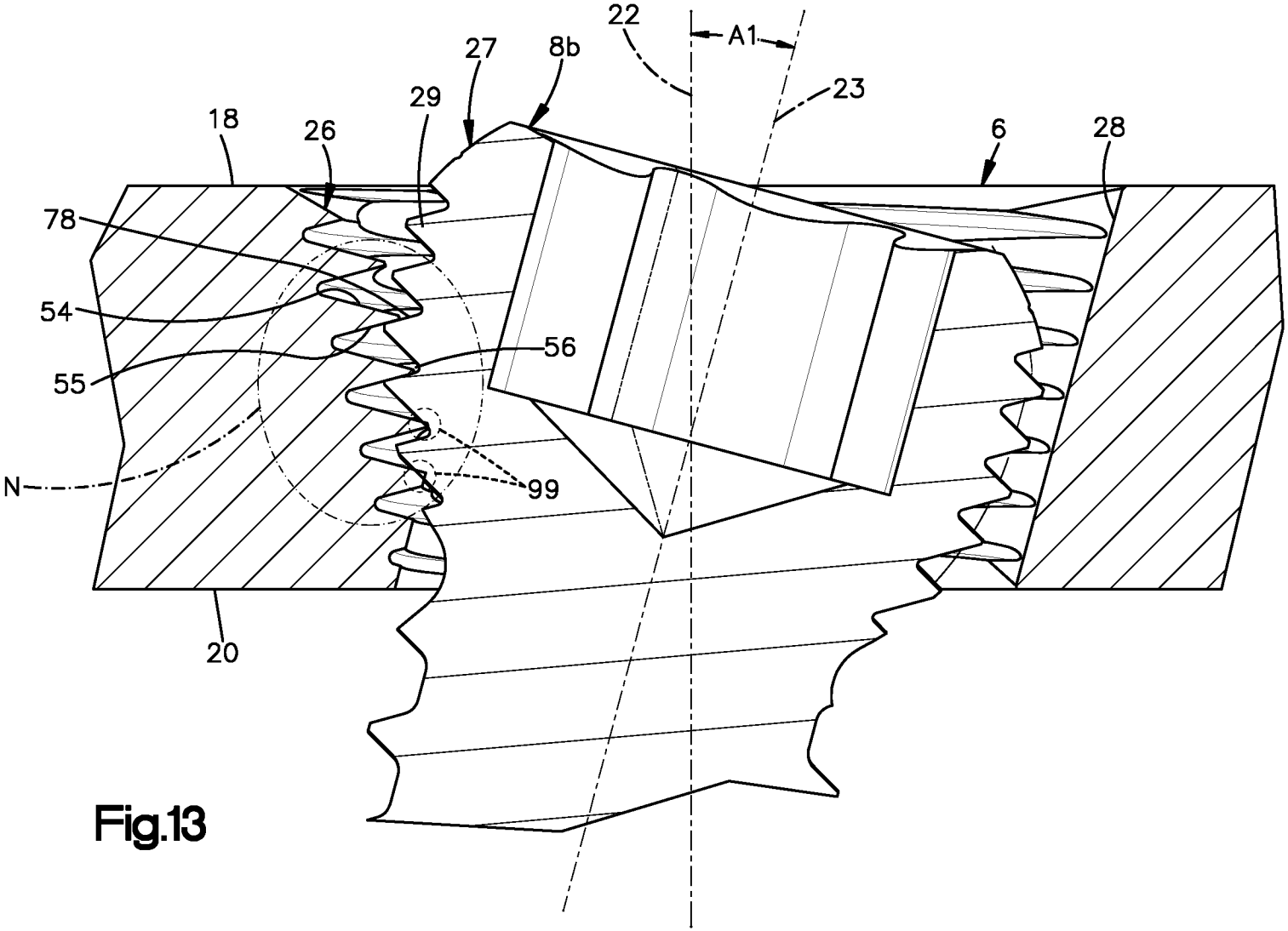
FIG. 13 is a sectional side view of the head of the VA locking screw of FIG. 8 during locking at an angulation of 15 degrees within the locking hole shown in FIG. 6.
Figure 14:
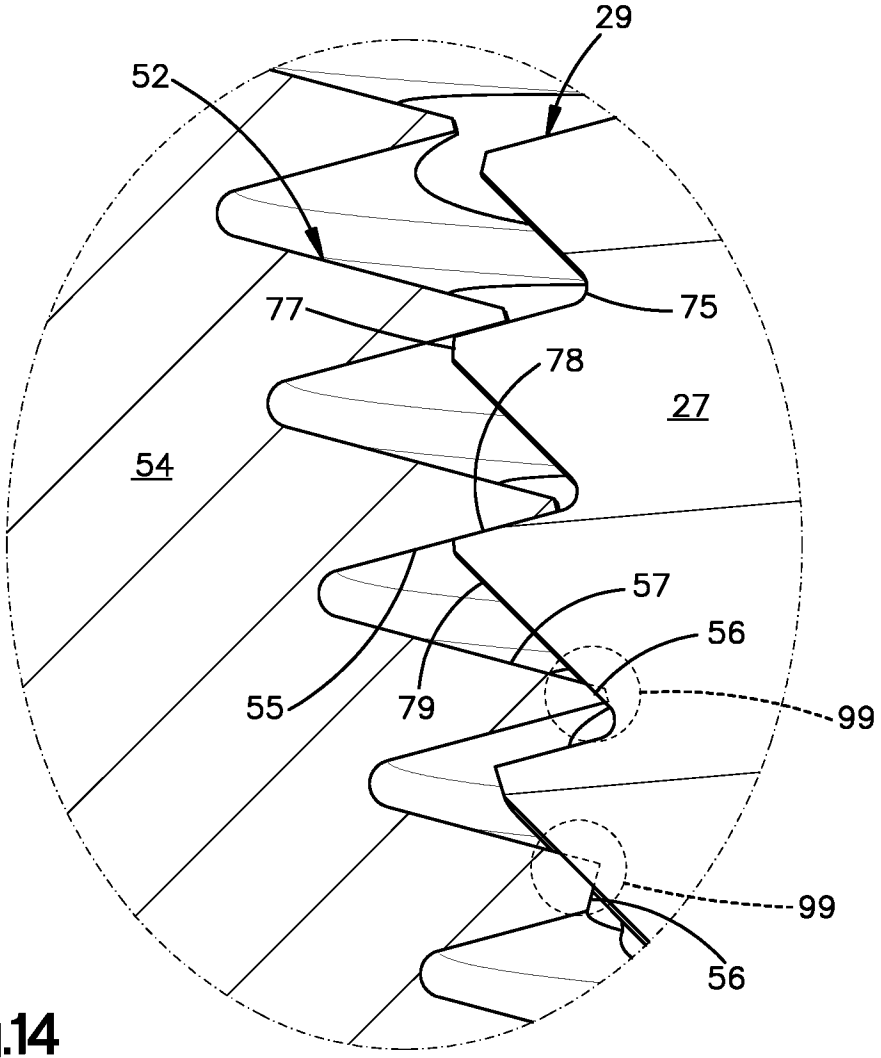
FIG. 14 is an enlarged view of region N in FIG. 13, showing deformation of the internal threads of the locking structure against the external threads on the head of the VA locking screw during locking.

Referring now to FIGS. 13 and 14, the VA locking hole 6 can be configured such that, when the VA locking screw 8b is inserted at an angulation of about 15 degrees with the screw shaft 25 extending toward a column 26, the upper surface 55 of the column threads 54 of the column 26 can be substantially parallel with the upper surfaces 78 of associated ones of the screw head threads 29. Such cooperative thread orientations can occur when the column thread angle A6 is about 30 degrees and the screw head thread angle is about 60 degrees. As described above, the crest centerline angle A3 and the thread depth D can cooperate with the column thread angle A6 to increase the clearance between the screw head thread crests 77 and the roots 58 of the column threads 54. Additionally, at the illustrated angulation, contact between the column threads 54 and the screw head threads 29 can occur predominantly at, or at least proximate, the column thread crests 56. As shown in FIG. 14, respective ones of the column thread crests 56 can deform against portions of the screw head threads 29 at interference regions 99 in a manner providing locking engagement with the screw head 27.

Figure 15:
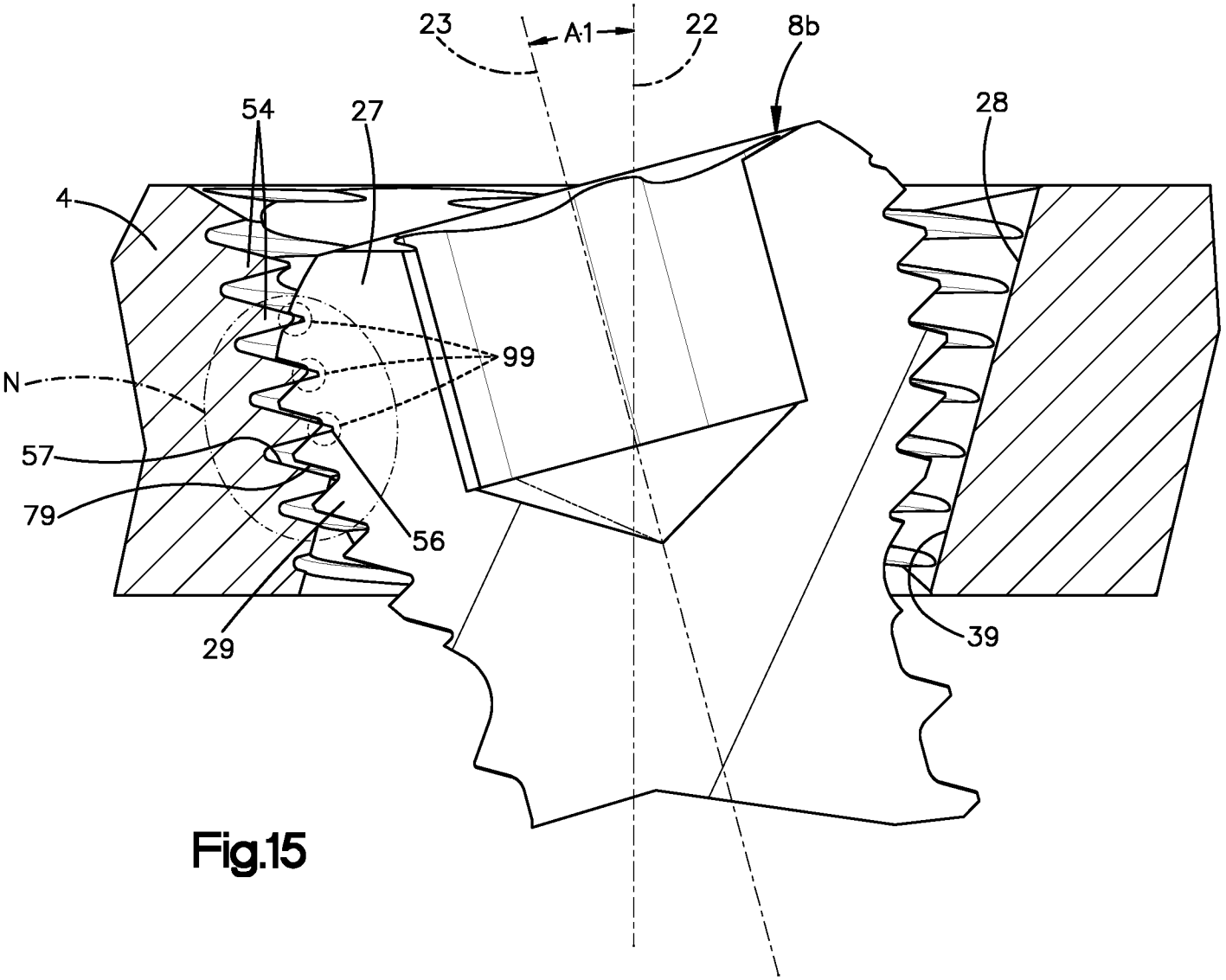
FIG. 15 is a sectional side view of the head of the VA locking screw of FIG. 8 during locking at an opposite angulation of 15 degrees within the locking hole shown in FIG. 6.
Figure 16:
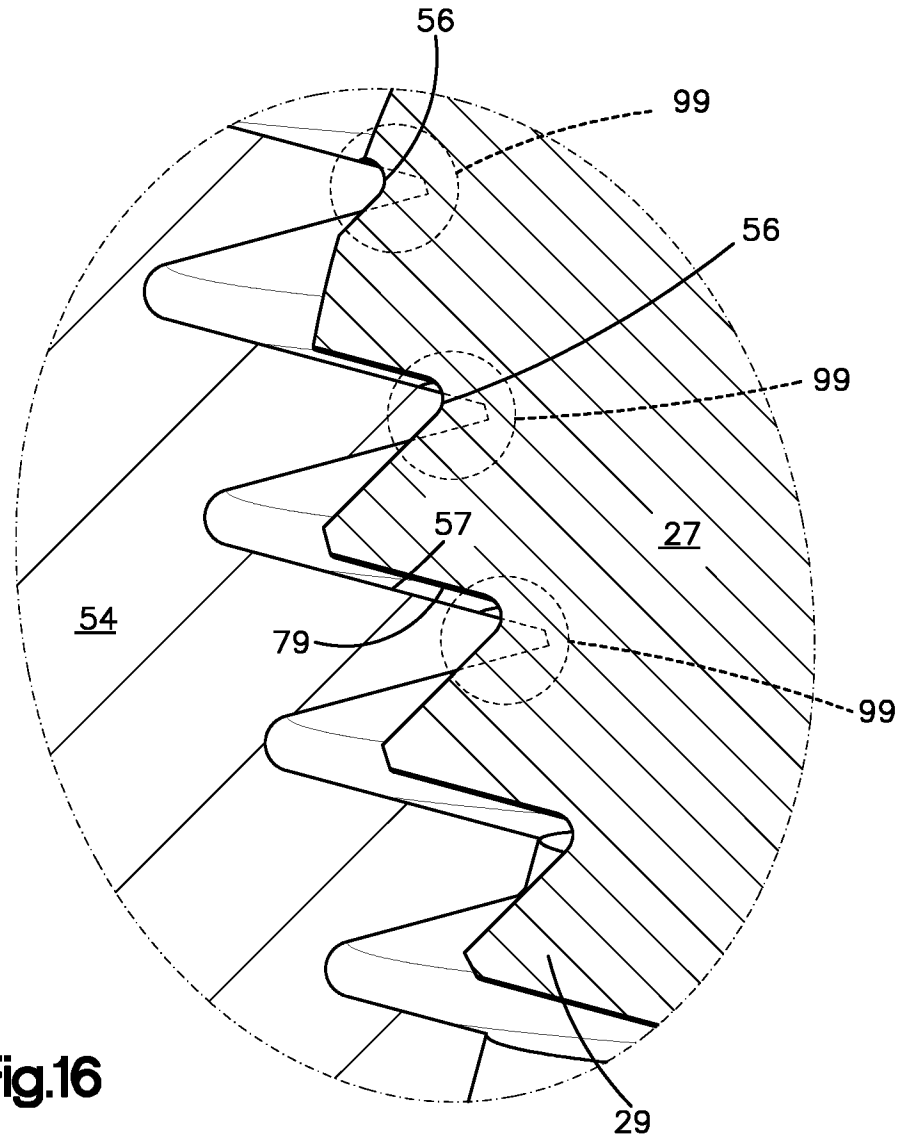
FIG. 16 is an enlarged view of region N in FIG. 15, showing deformation of the internal threads of the locking structure against the external threads on the head of the VA locking screw during locking.

Referring now to FIGS. 15 and 16, the VA locking hole 6 can be configured such that, when the VA locking screw 8b is inserted at an angulation of about 15 degrees with the screw shaft 25 extending toward the trough 39 of a recess 28 opposite a column 26, the lower surface 57 of the column threads 54 of the column 26 can be substantially parallel with the lower surfaces 79 of associated ones of the screw head threads 29. As before, the crest centerline angle A3 and the thread depth D can cooperate with the column thread angle A6 to increase the clearance between the screw head thread crests 77 and the roots 58 of the column threads 54. Additionally, at the illustrated angulation, contact between the column threads 54 and the screw head threads 29 can occur predominantly at or at least proximate the column thread crests 56. As shown in FIG. 16, respective ones of the column thread crests 56 can deform against portions of the screw head threads 29 at interference regions 99 in a manner providing locking engagement with the screw head 27.

It is to be appreciated that one or more of the characteristics of the columns 26, such as, by way of non-limiting example, the crest centerline angle A3, the mean radii R2, R3, R4, the thread angle A6, the thread depth D, the thread pitch P, and the thread lead L can be tailored as needed to provide desired locking characteristics. For example, adjustments to the thread geometry that reduce the form-fit can be offset by adjustments that increase the radial deformation of the column threads 54, and vice versa.

With reference to FIGS. 17 through 23, additional embodiments of the VA locking holes 6 will now be described. For the sake of brevity, the following description will focus primarily on the differences between these embodiments and the embodiments described above with reference to FIGS. 1 through 16. Although the following description focuses on a single threaded column 26, it is to be appreciated that the description can apply to the other columns 26 in the VA locking hole 6.

Figure 17:
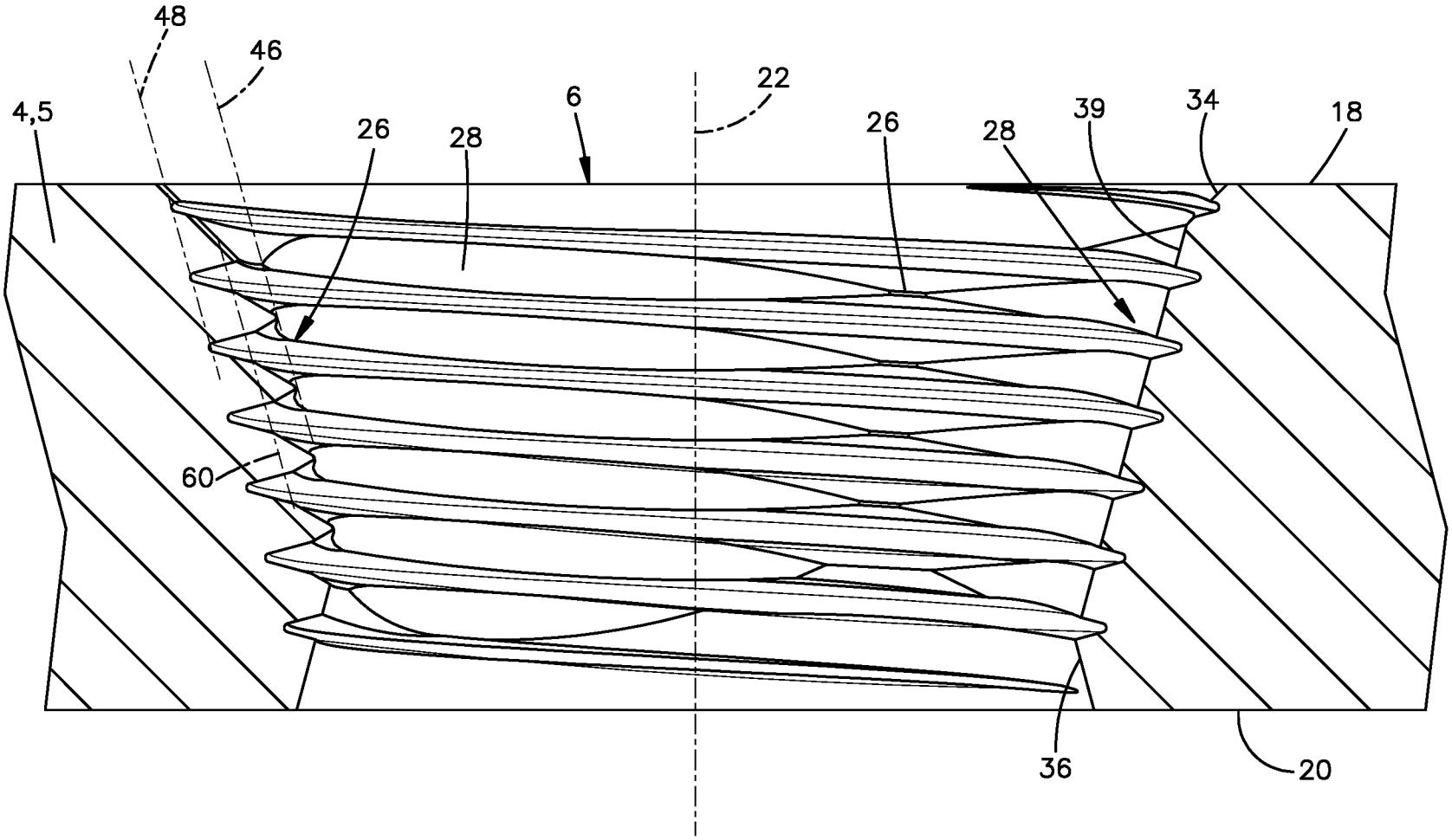
FIG. 17 is a side sectional view of a locking hole, according to another embodiment of the present disclosure.
Figure 18:
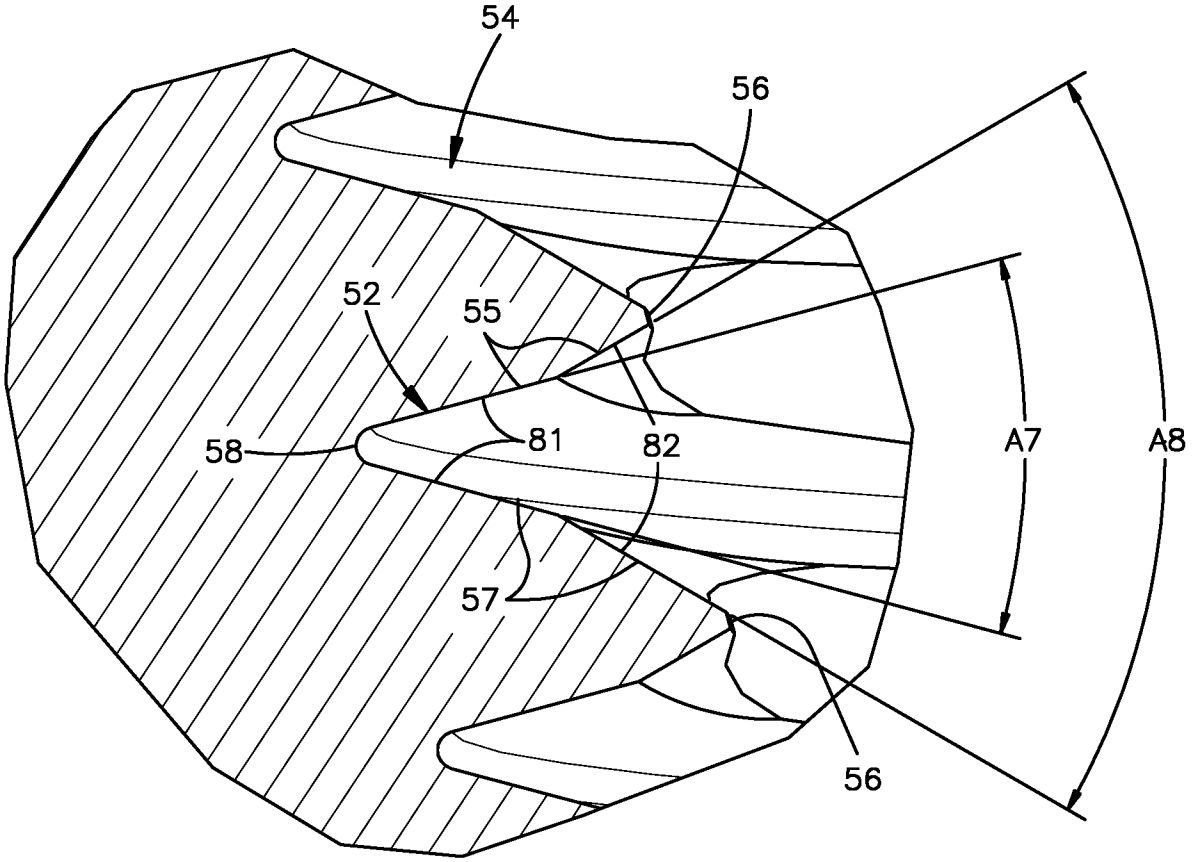
FIG. 18 is a sectional profile view of internal threads of the locking hole shown in FIG. 17.

Referring now to FIGS. 17 and 18, in another embodiment, the column threads 54 can define multiple thread angles. For example, the first and second thread surfaces 55, 57 of each thread segment 52 can each define a first portion 81 and a second portion 82. The first portions 81 of the first and second thread surfaces 55, 57 can extend from the root 58 to the respective second portions 82. The second portions 82 can extend from the respective first portions 81 toward the respective crests 56. The axial space between the first portions 81 can be referred to as the "root depression." In this embodiment, the axial space between the second portions 82 can be referred to as the "crest region." The first portions 81 can define a first thread angle A7 and the second portions 82 can define a second thread angle A8. The first thread angle A7, which can also be referred to as the "root depression angle," can be in a range of about 20 degrees to about 40 degrees, or about 25 degrees to about 35 degrees. The second thread angle A8 can be in a range of about 45 degrees to about 90 degrees. As shown, the first thread angle A7 can be about 30 degrees and the second thread angle A8 can be about 60 degrees. The column threads 54 of this embodiment can be characterized as "dual-angle" threads.

In the present embodiment, the column 26 design can optionally be substantially similar to that described with reference to FIGS. 6 and 7, with the primary difference being that the crests 56 of the present example are truncated with respect to those shown in FIGS. 6 and 7. Stated differently, one way of providing the column 26 shown in FIGS. 16 and 17 is to begin with the columns 26 shown in FIGS. 6 and 7 and remove body 4 material at the crests 56 thereof in a manner increasing the crest mean radius R2 and forming thread portions 82 at the second thread angle A8. Thus, the thread depth D in the present embodiment can be shallower than in those described above. To compensate for this, the crest centerline 46 can optionally be located radially further from the central hole axis 22 than in the above embodiments, because less deformation will occur at the thread crests 56.

Figure 21:
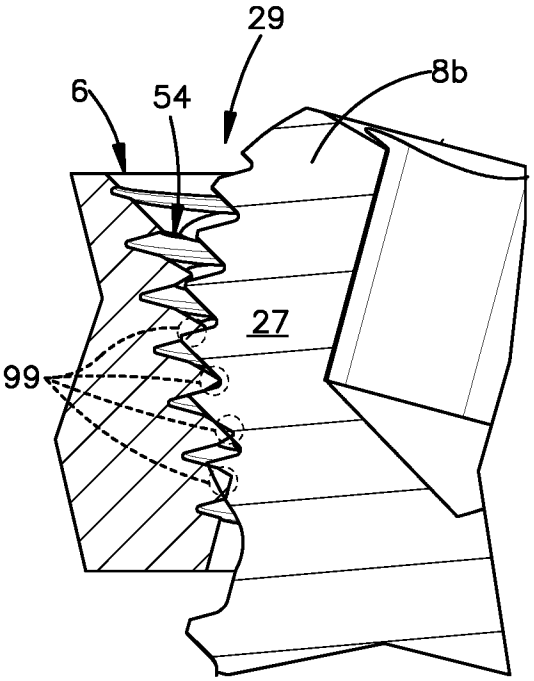
FIG. 21 is a partial sectional side view of the head of the VA locking screw locked at an opposite angulation of 15 degrees within the locking hole shown in FIG. 17.
Figure 20:
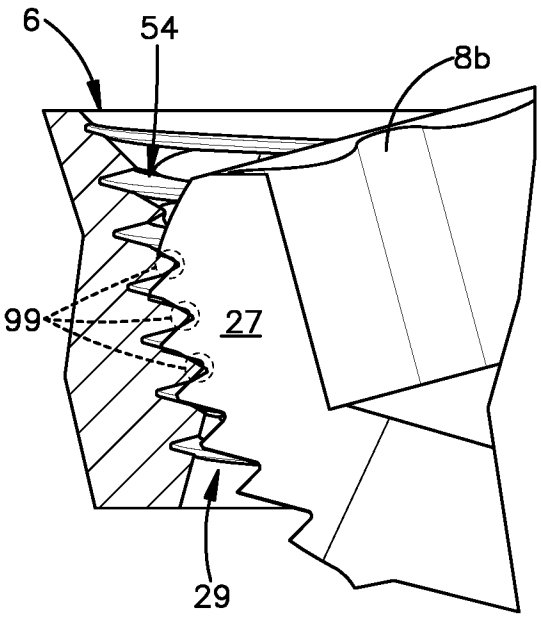
FIG. 20 is a partial sectional side view of the head of the VA locking screw locked at an angulation of 15 degrees within the locking hole shown in FIG. 17.
Figure 19:
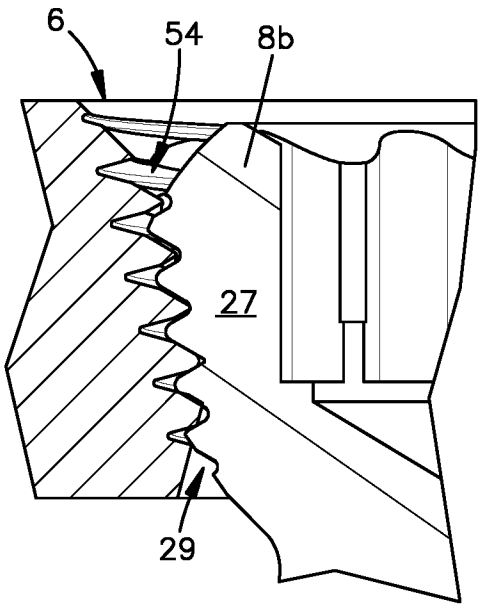
FIG. 19 is a partial sectional side view of the head of the VA locking screw of FIG. 8 locked at a nominal orientation within the locking hole shown in FIG. 17.

As shown in FIGS. 19 through 21, the geometry of the dual-angle column threads 54, particularly at the crest regions, can provide an increased form-fit relative to the embodiments described above. For example, at a nominal angulation, as shown in FIG. 19, the threaded locking engagement can be substantially entirely via form-fit. The geometry at the root depressions can provide clearance between the column thread roots 58 and the head thread crests 77 at various angulations. The root depression can also provide the column threads 54 with axial deformability, which allows the column threads 54 to deform downward or upward, such as when the VA locking screw 8b is inserted with timing error, for example. However, in the present embodiment, the axial deformability can be less profound at the crests 56 than in the above embodiments. As shown in FIGS. 20 and 21, at angulations of 15 degrees away and toward the column 26, the column threads 54 can deform radially outward at interference regions 99 so as to achieve a locking press-fit with the screw head 27.

Figure 22:
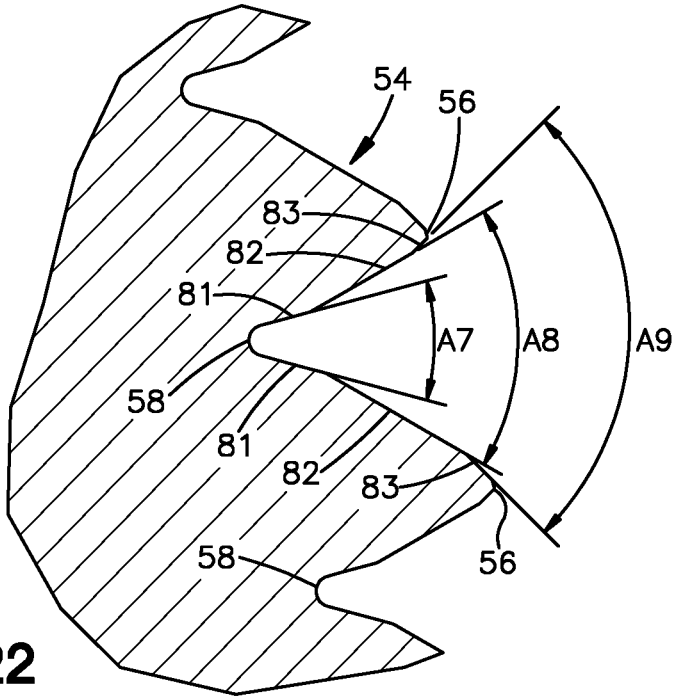
FIG. 22 is a sectional profile view of internal threads of a locking hole, according to another embodiment of the present disclosure.

Referring now to FIG. 22, in further embodiments, column threads 54 can define a third thread angle A9. For example, the first and second thread surfaces 55, 57 of the thread segments 52 can each define a third portion 83 extending from the respective second portions 82 to the respective crests 56. In this embodiment, the axial space between the third portions 83 can be referred to as the "crest region." The third thread angle A9 can be in a range of about 70 degrees up to about 179 degrees, or about 80 degrees to about 100 degrees. In one example embodiment, the first thread angle A7 can be about 30 degrees, the second thread angle A8 can be about 60 degrees, and the third thread angle A9 can be about 90 degrees.

Figure 23:
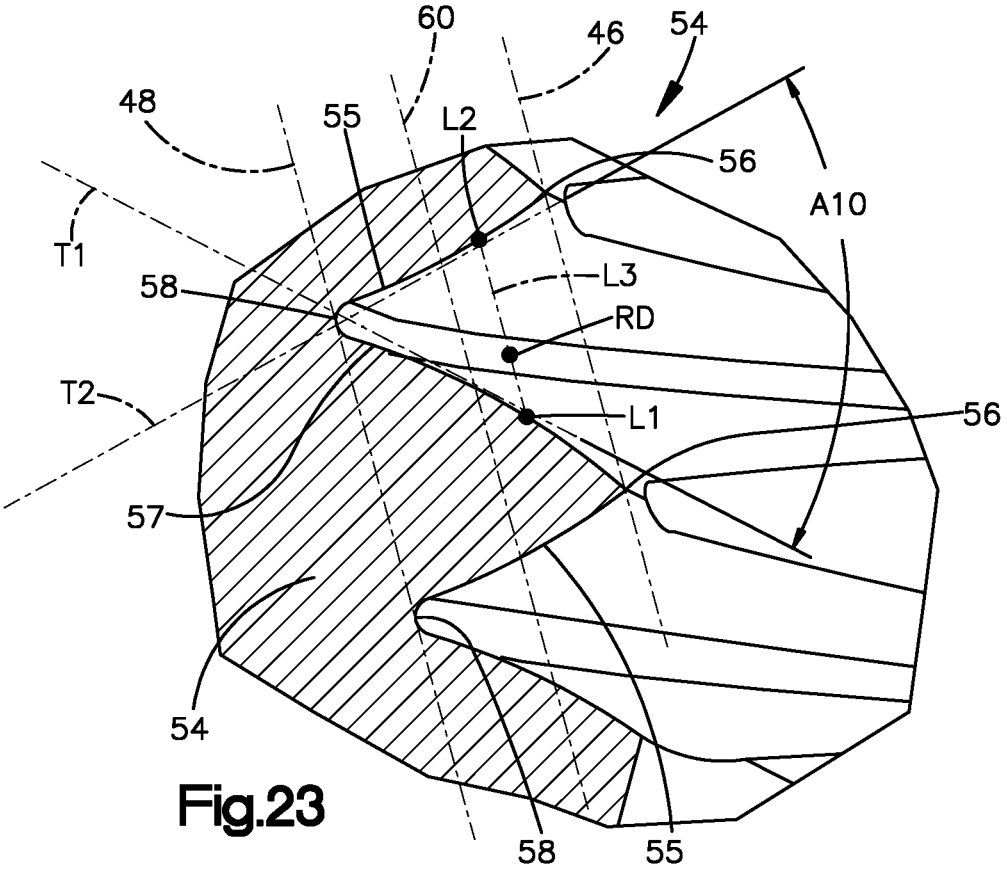
FIG. 23 is a sectional profile view of internal thread of a locking hole, according to another embodiment of the present disclosure.

Referring now to FIG. 23, the column threads 54 can optionally define an arcuate profile in a reference plane containing the crest centerline 46 and the central hole axis 22. For example, the first and second thread surfaces 55, 57 can each extend radially inward from the root centerline 48 to the crest centerline 46 along an arcuate profile path, such as an involute profile path, by way of a non-limiting example. In this manner, the columns threads 54 of the present embodiment define a varying thread angle A10 between the root and crest centerlines 48, 46. The varying thread angle A10 at any radial location RD between the root and crest centerline 48, 46 can be defined as follows: the varying thread angle A10 is the angle between a pair of tangent lines T1, T2 intersecting the first and second thread surfaces 55, 57 at respective locations L1, L2 along a reference line L3 parallel with the thread midline 60 and coincident with the radial location RD. In such embodiments, the varying thread angle A10 can vary from an angle of about 5 degrees adjacent the root 58 to an angle A10 of about 179 degrees as the crests 56, for example.

While the embodiments shown in FIGS. 22 and 23 have less axial deformability than other embodiments disclosed herein, they provide better form fit and less plastic and elastic deformation.

Figure 24:
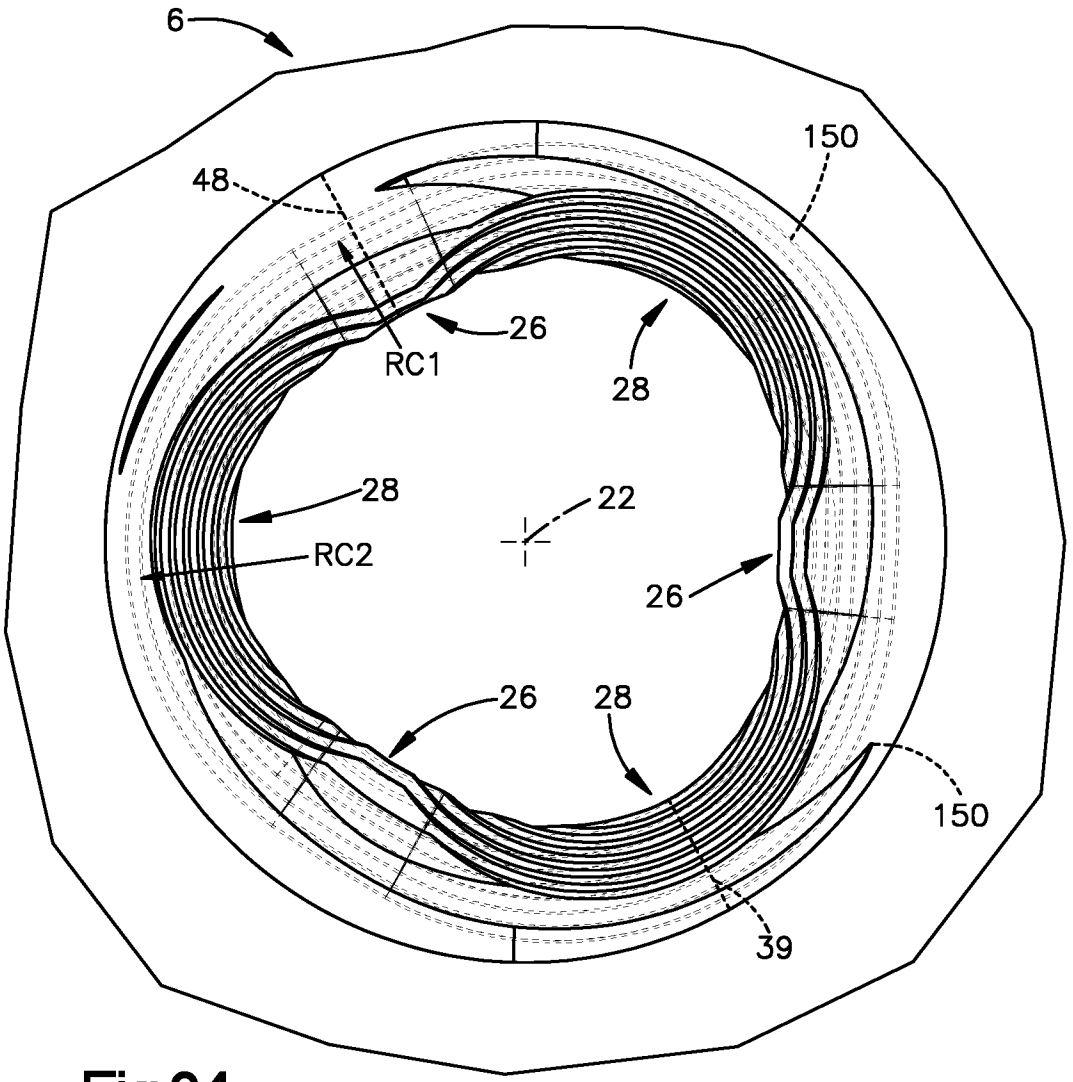
FIG. 24 is a top plan view of a locking hole, according to another embodiment of the present disclosure, wherein a thread path of the roots of the internal threading is shown.

Referring now to FIG. 24, in additional embodiments, the roots 58 of the hole threads 9 can follow a root thread path 150 that is different than the thread path followed by the crests 56. In particular, the root thread path 150 can revolve about the central hole axis 22 so as to define a non-circular spline profile in a reference plane orthogonal to the central hole axis 22. In one such example, the radius of curvature of the spline, as viewed in the reference plane, is greater at the columns 26 (RC1) than at locations remote from the columns 26 (RC2), such as at the recess troughs 39, for example. Stated differently, in this example the root thread path 150 follows a polyconic spline, wherein the curvature of the root thread path 150 "flattens out" at the columns 26, such as at the root centerline 48. Thus, within the columns 26, any contact between a screw head thread crest 77 and the thread root 58 becomes more tangential. In this manner, cross-threading within the columns 26 can be further reduced or avoided.

Figure 25:
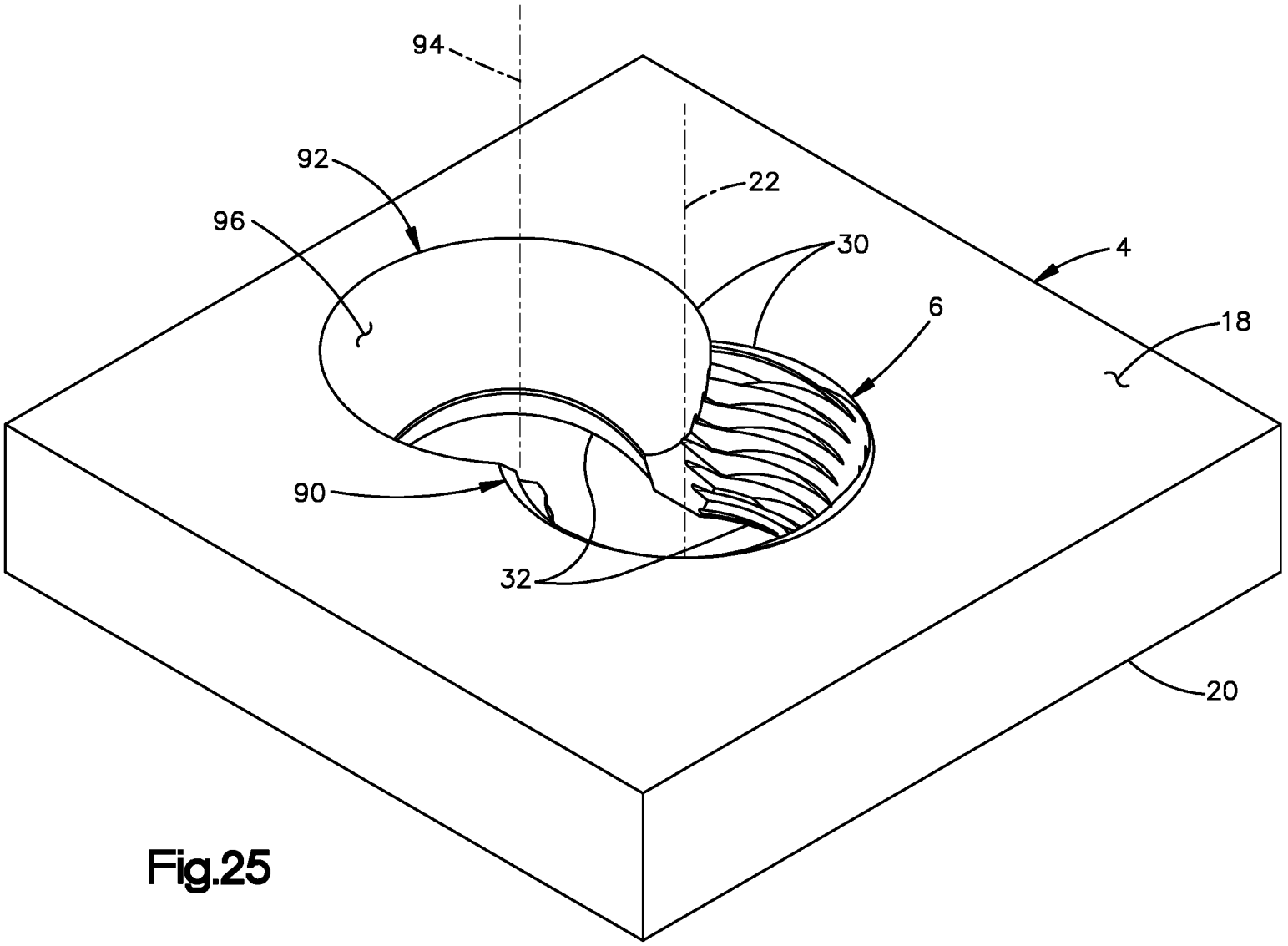
FIG. 25 is a perspective view of a bone plate having a combination hole that includes a variable angle locking hole as illustrated in FIG. 3 and a compression hole that is open to the variable angle locking hole portion.
Figure 26:
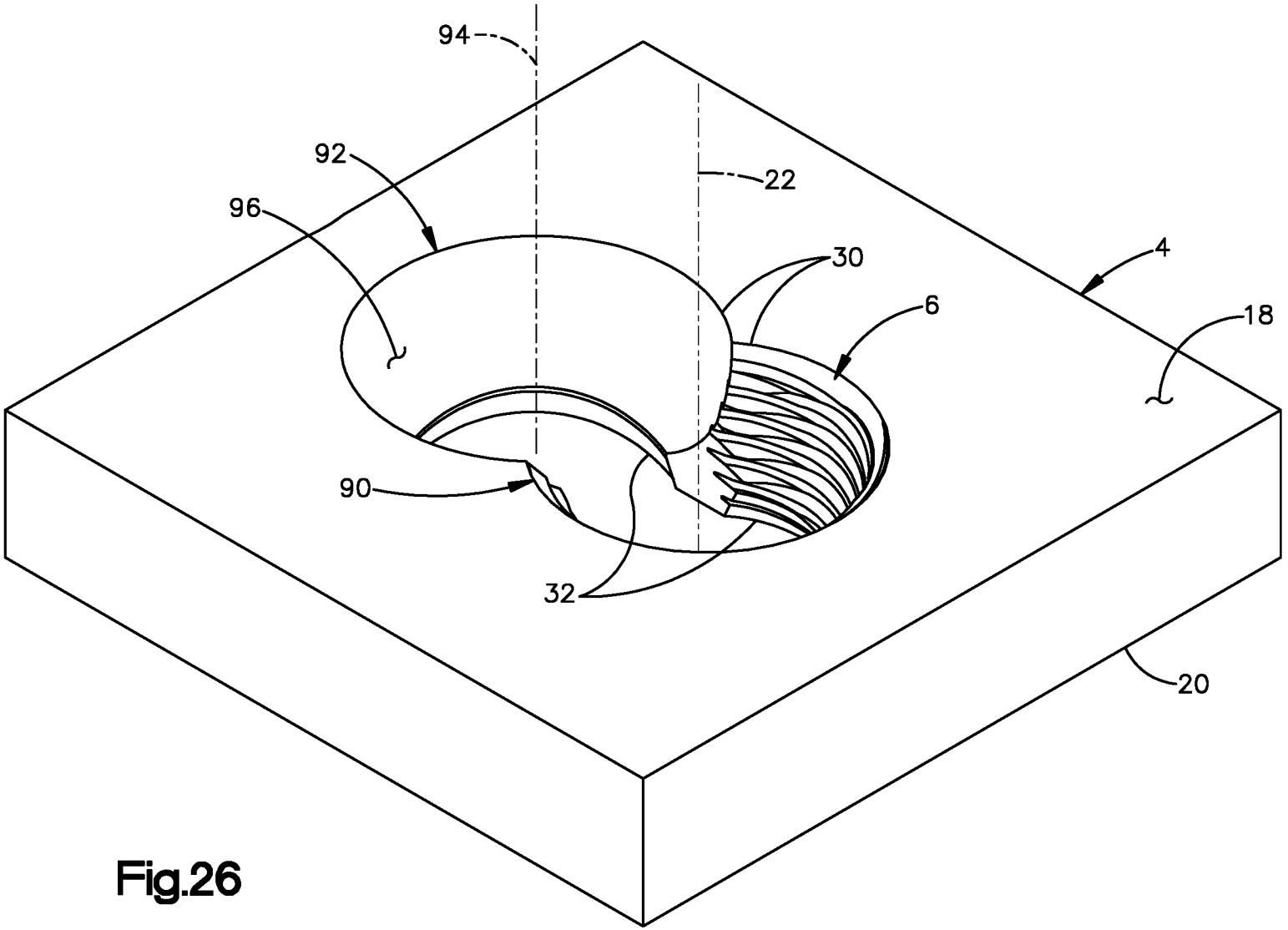
FIG. 26 is a perspective view of a bone plate having a combination hole that includes a variable angle locking hole as illustrated in FIG. 17 and a compression hole that is open to the variable angle locking hole portion.

Referring now to FIGS. 25 through 26, the bone plate 4 can include a combination hole 90 (also referred to as a "combi-hole") that includes one of the VA locking holes 6 described above in combination with a compression hole 92. Thus, the interior surface 24 of the combination hole 90 can define both the VA locking hole 6 and the compression hole 92, each extending from the upper plate surface 18 to the lower plate surface 22. The VA locking hole 6 and the compression hole 92 of the combination hole 90 can be open to each other along a direction that is perpendicular to one or both of the central hole axis 22 of the VA locking hole 6 and a central hole axis 94 of the compression hole 92. The central hole axis 22 of the VA locking hole 6 and the central hole axis 94 of the compression hole 92 of the combination hole 90 can be aligned with each other along the longitudinal direction L, or along any suitable alternative direction as desired.

The interior surface 24 of the bone plate 4 can thus also define a compression surface 96 of the compression hole 92 of the combination hole 90. Thus, the upper perimeter 30 can define an upper opening to each of the VA locking hole 6 and the unthreaded compression hole 92 that is open to the VA locking hole 6. Similarly, the lower perimeter 32 can define a lower opening to each of the VA locking hole 6 and the unthreaded compression hole 92 that is open to the VA locking hole 6.

At least a portion up to an entirety of the compression surface 96 can be unthreaded. Accordingly, the unthreaded compression head of a compression screw is configured to bear against the bone plate 4, and in particular the compression surface 96, in the compression hole 92 so as to apply a compressive force against the bone plate 4 toward the underlying bone 100.

In one example, the compression surface 96 can be concave in the axial direction with respect to the central hole axis 94 of the compression hole 92. For instance, the compression surface 96 can be dish shaped or spherical. Thus, the compression surface 96 can be configured to be placed in surface contact with the compression head of the compression screw. Alternatively, the compression surface 96 can be linear in the axial direction as it tapers radially inwardly toward the central hole axis 94. Additional details of the combination hole 90, as well as operation of the compression screw in the combination hole, can be according to the descriptions set forth in U.S. patent application Ser. Nos. 15/926,390 and 15/940,761, referenced above.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone plate comprising:

an upper surface configured to face away from a bone and an opposed lower surface configured to face the bone; and at least one hole extending through the bone plate from the upper surface to the lower surface along a central hole axis, the central hole axis oriented along an axial direction, the at least one hole defined by an interior surface of the bone plate, the interior surface further defining a plurality of columns sequentially located about a circumference of the interior surface and a plurality of recesses located circumferentially between the columns, wherein each of the columns defines a plurality of thread segments, wherein each of the thread segments defines a root, a first thread surface extending from the root to a first crest, a second thread surface extending from the root to a second crest, and at least a portion of the first and second thread surfaces are offset from one another at a thread angle, and wherein the thread angle of at least one of the thread segments is in a range of 20 degrees to 40 degrees.

2. The bone plate of claim 1, wherein the thread angle is in the range of 25 degrees to 35 degrees.

3. The bone plate of claim 2, wherein, in each of the plurality of columns, the first and second crests of at least a majority of the thread segments are coincident with a centerline of the respective column, wherein the centerline extends along a plane that includes the central hole axis.

4. The bone plate of claim 3, wherein the centerline is oriented at a first angle relative to the central hole axis, and the first angle is in a range of about 10 degrees to about 20 degrees.

5. The bone plate of claim 3, wherein the pluralities of thread segments of the columns extend along one or more helical paths.

6. The bone plate of claim 5, wherein the one or more helical paths comprise a double-lead helical path.

7. The bone plate of claim 6, wherein at least one of the thread segments defines a thread pitch between the respective first and second crests along the axial direction, and one or both of the respective first and second crests is configured to deflect, non-destructively, up to a distance along the axial direction equivalent to one half of the thread pitch.

8. The bone plate of claim 5, wherein the one or more helical paths are coincident with at least one of the first and second crests of each thread segment, and the root of each thread segment extends along a second path about the central hole axis, wherein a radius of curvature of the second path is greater at the columns than at locations remote from the columns.

9. The bone plate of claim 2, wherein:

the first and second thread surfaces each defines a first portion and a second portion, the first portion extending from the root to the second portion, the second portion extending from the first portion toward the respective first or second crest; and the thread angle is a first thread angle measured between the respective first portions; and the respective second portions are offset from one another at a second thread angle that is different than the first thread angle.

10. The bone plate of claim 9, wherein the second thread angle is in a range of about 45 degrees to about 90 degrees.

11. The bone plate of claim 9, wherein the first thread angle is about 30 degrees and the second thread angle is about 60 degrees.

12. The bone plate of claim 9, wherein:

the first and second thread surfaces each defines a third portion extending from the second portion to the respective first or second crest; and the respective third portions are offset from one another at a third thread angle that is different than the second thread angle.

13. The bone plate of claim 12, wherein the third thread angle is in a range of about 70 degrees to about 179 degrees.

14. The bone plate of claim 12, wherein the first thread angle is about 30 degrees, the second thread angle is about 60 degrees, and the third thread angle is about 90 degrees.

15. The bone plate of claim 12, wherein the first and second thread surfaces each extend along a respective involute curve between the root and the respective first or second crest, the first and second thread surfaces define a varying thread angle, and the varying thread angle varies in a range from about 5 degrees adjacent to the root to 179 degrees at the crests.

16. The bone plate of claim 1, wherein at least one crest of each column is configured to deform outward *away* from the central hole axis along a radial direction that is perpendicular to the axial direction responsive to threaded engagement with at least one thread of a locking screw inserted within the at least one hole.

17. The bone plate of claim 1, wherein the plurality of columns comprises three columns, and the plurality of recesses comprises three recesses.

18. The bone plate of claim 17, wherein each of the recesses defines a recess axis spaced from the central hole axis along a radial direction that is perpendicular to the axial direction, and each recess axis is parallel with the central hole axis.

19. The bone plate of claim 18, wherein the recess axes are equidistant from the central hole axis, and each recess defines a portion of a frusto-conical shape having a central cone axis coincident with the respective recess axis, wherein the frusto-conical shape is the frustum of a right circular cone.

20. The bone plate of claim 19, wherein the at least one hole intersects another hole, and the at least one hole and the another hole collectively define a combination hole.

*21. A bone plate comprising:*

*an upper surface configured to face away from a bone and an opposed lower surface configured to face the bone; and*

*at least one hole extending through the bone plate from the upper surface to the lower surface along a central hole axis, the central hole axis oriented along an axial direction, the at least one hole defined by an interior surface of the bone plate, the interior surface further defining a plurality of columns sequentially located about a circumference of the interior surface, wherein each of the columns defines a plurality of thread segments,*

*wherein each of the thread segments defines a root, a first thread surface extending from the root to a first crest, a second thread surface extending from the root to a second crest, and at least a portion of the first and second thread surfaces are offset from one another at a thread angle, and*

*wherein the thread angle of at least one of the thread segments is in a range of 20 degrees to 40 degrees.*

*22. The bone plate of claim 21, wherein the thread angle is in the range of 25 degrees to 35 degrees.*

*23. The bone plate of claim 22, wherein, in each of the plurality of columns, the first and second crests of at least a majority of the thread segments are coincident with a centerline of the respective column, wherein the centerline extends along a plane that includes the central hole axis.*

*24. The bone plate of claim 23, wherein the centerline is oriented at a first angle relative to the central hole axis, and the first angle is in a range of about 10 degrees to about 20 degrees.*

*25. The bone plate of claim 23, wherein the pluralities of thread segments of the columns extend along one or more helical paths.*

*26. The bone plate of claim 25, wherein the one or more helical paths comprise a double-lead helical path.*

*27. The bone plate of claim 26, wherein at least one of the thread segments defines a thread pitch between the respective first and second crests along the axial direction, and one or both of the respective first and second crests is configured to deflect, non-destructively, up to a distance along the axial direction equivalent to one half of the thread pitch.*

*28. The bone plate of claim 25, wherein the one or more helical paths are coincident with at least one of the first and second crests of each thread segment, and the root of each thread segment extends along a second path about the central hole axis, wherein a radius of curvature of the second path is greater at the columns than at locations remote from the columns.*

*29. The bone plate of claim 21, wherein at least one crest of each column is configured to deform outward away from the central hole axis along a radial direction that is per-*

*pendicular to the axial direction responsive to threaded engagement with at least one thread of a locking screw inserted within the at least one hole.*

*30. A bone plate comprising:*

*an upper surface configured to face away from a bone and an opposed lower surface configured to face the bone; and*

*a hole extending through the bone plate from the upper surface to the lower surface, the hole defined by an interior surface of the bone plate, the interior surface further defining a plurality of threaded columns sequentially located about a circumference of the interior surface,*

*wherein the threaded columns comprise threading that defines a root, a first thread surface extending from the root to a first crest, a second thread surface extending from the root to a second crest, and at least a portion of the first and second thread surfaces are offset from one another at a thread angle that is in a range of 20 degrees to 40 degrees.*

*31. The bone plate of claim 30, wherein the columns are evenly spaced about the hole.*

*32. The bone plate of claim 30, wherein the thread angle is in the range of 25 degrees to 35 degrees.*

*33. The bone plate of claim 30, wherein the thread angle is about 30 degrees.*

*34. The bone plate of claim 30, wherein the threading is helical.*

*35. The bone plate of claim 30, wherein the threading defines a thread pitch between the respective first and second crests, and one or both of the respective first and second crests is configured to deflect, non-destructively, up to a distance along the axial direction equivalent to one half of the thread pitch.*

*36. The bone plate of claim 30, wherein at least one crest of the threading of each of the threaded columns is configured to radially deform in response to a threaded engagement with at least one thread of a locking screw inserted within the hole.*

* * * * *